(12) United States Patent
Kobayashi et al.

(10) Patent No.: US 9,371,301 B2
(45) Date of Patent: Jun. 21, 2016

(54) PRENYLARENE COMPOUND AND USE THEREOF

(75) Inventors: Motomasa Kobayashi, Osaka (JP); Naoyuki Kotoku, Osaka (JP); Masayoshi Arai, Osaka (JP); Takashi Kawachi, Osaka (JP)

(73) Assignee: Osaka University, Osaka (JP)

( * ) Notice: Subject to any disclaimer, the term of this patent is extended or adjusted under 35 U.S.C. 154(b) by 777 days.

(21) Appl. No.: 13/696,425

(22) PCT Filed: May 6, 2011

(86) PCT No.: PCT/JP2011/060578
§ 371 (c)(1),
(2), (4) Date: Nov. 30, 2012

(87) PCT Pub. No.: WO2011/138956
PCT Pub. Date: Nov. 10, 2011

(65) Prior Publication Data
US 2013/0065937 A1    Mar. 14, 2013

(30) Foreign Application Priority Data

May 7, 2010  (JP) ................................ 2010-107749

(51) Int. Cl.
| C07D 307/36 | (2006.01) |
| --- | --- |
| C07D 333/06 | (2006.01) |
| A61K 31/341 | (2006.01) |
| A61K 31/381 | (2006.01) |
| A61K 45/06 | (2006.01) |
| C07D 333/08 | (2006.01) |

(52) U.S. Cl.
CPC ............ *C07D 307/36* (2013.01); *A61K 31/341* (2013.01); *A61K 31/381* (2013.01); *A61K 45/06* (2013.01); *C07D 333/08* (2013.01)

(58) Field of Classification Search
None
See application file for complete search history.

(56) References Cited

PUBLICATIONS

Venkateswarlu et al. "Three New Heptaprenylhydroquinone Derivatives From the Sponge *Ircinia fasciculata*". Journal of Natural Products. Sep. 1994; 57(9):1286-1289.*
Tziveleka et al. "Marine Polyprenylated Hydroquinones, Quinones, and Chromenols with Inhibitory Effects on Leukotriene Formation". Chemistry & Biodiversity. 2005; 2(7):901-909.*
Extended European Search Report issued Jan. 2, 2014 in corresponding Application No. 11 77 7475.2.
Arai et al., "Hypoxia-Selective Growth Inhibition of Cancer Cells by Furospinosulin-1, a Furanosesterterpene Isolated from an Indonesian Marine Sponge", Journal of Chem. Med. Chem., 2010, vol. 5, pp. 1919-1926.
Erdogan-Orhan et al., "Polyprenyl-Hydroquinones and -Furans from Three Marine Sponges Inhibit the Cell Cycle Regulating Phosphatase CDC25A", Journal of Natural Product Research, 2004, vol. 18, No. 1, pp. 1-9.
Tasdemir et al., "Cytotoxic Bromoindole Derivatives and Terpenes from the Philippine Marine Sponge *Smenospongia* sp.", Journal of Biosciences, 2002, vol. 57, pp. 914-922.
Morimoto et al., "Ubiquinones and related substances. VIII Biological Behavior of ubichromenol in rats", Chemical and Pharmaceutical Bulletin, 1965, vol. 13, No. 10, pp. 1164-1167.
Liu et al., "Molecular-Targeted Antitumor Agents. 19. Furospongolide from a Marine *Lendenfeldia* sp. Sponge Inhibits Hypoxia-Inducible Factor-1 Activation in Breast Tumor Cells", Journal of Natural Products, 2008, vol. 71, No. 11, pp. 1854-1860.
Mao et al, "Lipophilic 2,5-Disubstituted Pyrroles from the Marine Sponge *Mycale* sp. Inhibit Mitochondrial Respiration and HIF-1 Activation", Journal of Natural Products, 2009, vol. 72, No. 11, pp. 1927-1936.
Kashiwagi et al., "A redox-silent analogue of tocotrienol inhibits hypoxic adaptation of lung cancer cells", Biochemical and Biophysical Research Communications, 2008, vol. 365, No. 4, pp. 875-881.
Qiu et al., "Sesterterpenoids from the Marine Sponge *Hyrtios erectus*", Journal of Natural Products, 2004, vol. 67, No. 5, pp. 921-924.

(Continued)

*Primary Examiner* — Leslie A. Royds Draper
(74) *Attorney, Agent, or Firm* — Wenderoth, Lind & Ponack, L.L.P.

(57) ABSTRACT

A compound represented by the general formula (C):

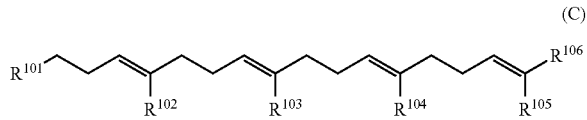

(C)

(wherein $R^{101}$ represents a substituted or unsubstituted aromatic heterocyclic group,
$R^{102}$, $R^{103}$, $R^{104}$ and $R^{105}$ may be the same or different, and each represents a hydrogen atom, a halogen atom, an alkyl group having 1 to 3 carbon atoms, or a haloalkyl group having 1 to 3 carbon atoms, and
$R^{106}$ represents a hydrogen atom, or a saturated or unsaturated hydrocarbon group which is a straight or branched chain having 1 to 12 carbon atoms, but
excluded is the case where $R^{101}$ is a 3-furyl group, $R^{102}$, $R^{103}$, $R^{104}$ and $R^{105}$ are all methyl groups, and $R^{106}$ is a methyl group, a 4-methyl-3-pentenyl group or a 4,8-dimethyl-3,7-nonadienyl group); or
a pharmaceutically acceptable salt thereof has selective inhibitory activity on hypoxic cell growth in a broad range of the concentration and therefore is useful as an active ingredient of a medicament for cancer prevention or treatment.

11 Claims, 5 Drawing Sheets

(56) References Cited

PUBLICATIONS

Cimino et al., "Polyprenyl derivatives from the sponge *Ircinia spinosula*. 2-polyprenylbenzoquinones, 2-polyprenylbenzoquinols, prenylated furans and A C-31 difuranoterpene", Tetrahedron, 1972, vol. 28, No. 5, pp. 1315-1324.

English translation of the International Preliminary Report on Patentability and Written Opinion dated Dec. 10, 2012.

Frederick S. Buckner et al., "Potent Anti-*Trypanosoma cruzi* Activities of Oxidosqualene Cyclase Inhibitors," Antimicrobial Agents and Chemotherapy, Apr. 2001, vol. 45, No. 4, pp. 1210-1215.

International Search Report issued Jun. 28, 2011 in International (PCT) Application No. PCT/JP2011/060578.

A. Giaccia et al., "HIF-1 as a Target for Drug Development", Nature Reviews Drug Discovery, vol. 2, 803, Oct. 2003.

K. Lee et al., "Hypoxia, Drug Therapy and Toxicity", Pharmacology & Therapeutics, vol. 113, pp. 229-246, 2007.

G. Powis et al., "Hypoxia Inducible Factor-1α as a Cancer Drug Target", Molecular Cancer Therapeutics, vol. 3, No. 5, pp. 647-654, 2004.

M. Arai et al., "Hypoxia Selective Cytotoxicity of Furospinosulin-1 From Indonesian Marine Sponge", Abstracts of 51st Symposium on the Chemistry of Natural Products, Nagoya, p. 647, 2009 (English abstract).

D. G. Nagle et al., "Marine Natural Products as Inhibitors of Hypoxic Signaling in Tumors", Phytochemistry Reviews, vol. 8, No. 2, pp. 415-429, 2009.

G. L. Semenza, "HIF-1 Inhibitors for Cancer Therapy: From Gene Expression to Drug Discovery", Current Pharmaceutical Design, vol. 15, Issue 33, pp. 3839-3843 (English abstract).

G. Melillo, "Hypoxia-Inducible Factor 1 Inhibitors", Methods in Enzymology, vol. 435, pp. 385-402, 2007.

S. Patiar et al., "Role of Hypoxia-Inducible Factor-1α as a Cancer Therapy Target", Endocrine-Related Cancer, vol. 13, Suppl. 1, pp. 61-75, 2006.

\* cited by examiner

PRENYLARENE COMPOUND AND USE THEREOF

This application is a U.S. national stage of International Application No. PCT/W2011/060578 filed May 6, 2011.

TECHNICAL FIELD

The present invention relates to a novel prenylarene compound and use thereof. More particularly, the present invention relates to a prenylarene compound which is useful for cancer prevention or treatment in that the compound exhibits cell-growth inhibitory activity in a hypoxia-selective manner by inhibiting insulin-like growth factor 2 expression.

BACKGROUND ART

Cancer combat is a great challenge for human beings, and to this end, chemotherapeutic drugs are still vigorously developed. However, the reality is that pharmaceuticals which have cancer cell-specific effects have not been created yet. Recently, it is known that the inside of tumors is partially hypoxic because neovascular network in tumors is disorderly formed from structurally fragile blood vessels. Since hypoxic cancer cells adapt to hypoxic conditions by metabolism alteration and actively produce proangiogenic factors and cancer metastasis-related factors, hypoxia is considered to greatly contribute to cancer aggravation.

HIF-1 (Hypoxia Inducible Factor-1) is known as a transcription factor which plays a crucial role in the hypoxic adaptation of cancer cells. HIF-1 functions as a heterodimer of an alpha subunit and a beta subunit, but under normal conditions, the alpha subunit is deficient because oxidative degradation of the alpha subunit is enhanced. Meanwhile, under hypoxia, the oxidative degradation is reduced and the two subunits form a heterodimer, which is an active-form HIF-1. The active-form HIF-1 increases the expressions of factors required for hypoxic adaptation and of angiogenesis- or metastasis-promoting factors by binding to HRE (hypoxia response element) in the respective promoter regions (see Non Patent Literature 1). Based on these findings as well as the facts that hypoxia is an environment specific to tumors and hardly exists under physiological conditions, many exploratory studies on compounds targeting HIF-1 or its related molecules have been carried out (see Non Patent Literature 2 and 3). However, since the whole mechanism for hypoxic adaptation of cancer cells has not been clarified, drug development based on other targets than HIF-1 or its related molecules has hardly been conducted. Moreover, no single pharmaceutical that inhibits HIF-1 or its related molecules has been marketed yet. As understood from the above, it is a crucial issue to create novel pharmaceuticals which are different in chemical structure and action mechanism from existing compounds.

Under such circumstances, the present inventors found that human prostate cancer DU-145 cells cultured under hypoxic conditions of the oxygen level of 1% can adapt to hypoxia via increased expression of HIF-1 alpha, and based on the use of these cells, constructed an assay system to screen for compounds which selectively inhibit cell growth under hypoxic conditions. By using the assay system, the present inventors screened various natural substance libraries, and as a result, found that the extract from a marine sponge inhabiting Indonesia has such an inhibitory activity. The present inventors fractionated and purified the extract using the activity test results as an indicator, and identified a substance having selective inhibitory activity on hypoxic cell growth, as furospinosulin-1, a furanosesterterpene represented by the following formula (see Non Patent Literature 4).

[Formula 1]

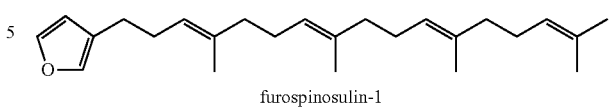

furospinosulin-1

The present inventors found that furospinosulin-1 not only inhibits in vitro cancer cell growth in a hypoxia-selective manner, but also significantly reduces in vivo tumor weight in mice subcutaneously inoculated with mouse sarcoma S180 cells as compared with the control. In addition, the present inventors revealed that the mechanism of these actions is based on the inhibition of hypoxia-inducible expression of insulin-like growth factor 2 (IGF-2), not on the inhibition of HIF-1 or its related molecules (see Non Patent Literature 4).

However, furospinosulin-1 at 1000 μM shows equal growth inhibitory activity against normoxic cells and hypoxic cells. Therefore, desired are novel compounds with higher safety, i.e., compounds which maintain hypoxic selectivity even in a high concentration.

CITATION LIST

Non Patent Literature

Non Patent Literature 1:
Nature Rev. Drug Discov., 2, 803, 2003
Non Patent Literature 2:
Pharmacol. Ther., 113, 229, 2007
Non Patent Literature 3:
Mol. Cancer. Ther., 3, 647, 2004
Non Patent Literature 4:
Arai et al., Symposium Papers of the 51st Symposium on the Chemistry of Natural Products in Nagoya, 647, 2009

SUMMARY OF INVENTION

Technical Problem

An object of the present invention is to provide a novel compound which has selective inhibitory activity on hypoxic cell growth in a broad range of the concentration, and to provide a medicament for cancer prevention or treatment comprising the compound as an active ingredient.

Solution to Problem

The present invention includes the following as a solution to the above-mentioned problems.

(1) A compound represented by the general formula (C):

[Formula 2]

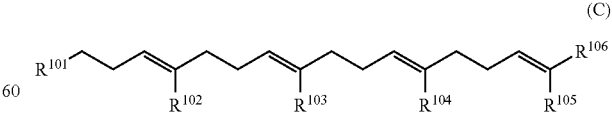

(wherein $R^{101}$ represents a substituted or unsubstituted aromatic heterocyclic group,
$R^{102}$, $R^{103}$, $R^{104}$ and $R^{105}$ may be the same or different, and each represents a hydrogen atom, a halogen atom, an alkyl group having 1 to 3 carbon atoms, or a haloalkyl group having 1 to 3 carbon atoms, and $R^{106}$ represents a hydrogen atom, or a saturated or unsaturated hydrocarbon group which is a straight or branched chain having 1 to 12 carbon atoms, but excluded is the case where $R^{101}$ is a 3-furyl group, $R^{102}$, $R^{103}$, $R^{104}$ and $R^{105}$ are all methyl groups, and $R^{106}$ is a methyl group, a 4-methyl-3-pentenyl group or a 4,8-dimethyl-3,7-nonadienyl group); or a pharmaceutically acceptable salt thereof.

(2) A compound represented by the general formula (I):

[Formula 3]

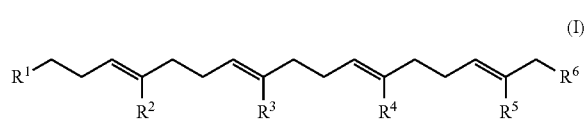

(wherein $R^2$ represents a substituted or unsubstituted aromatic heterocyclic group, $R^2$, $R^3$, $R^4$ and $R^5$ may be the same or different, and each represents a hydrogen atom, a halogen atom, an alkyl group having 1 to 3 carbon atoms, or a haloalkyl group having 1 to 3 carbon atoms, and $R^6$ represents a hydrogen atom or a prenyl group, but excluded is the case where $R^1$ is a 3-furyl group, and $R^2$, $R^3$, $R^4$ and $R^5$ are all methyl groups); or a pharmaceutically acceptable salt thereof.

(3) The compound according to the above (1), wherein $R^{106}$ is a methyl group, a 4-methyl-3-pentenyl group or a 3-butynyl group; or a pharmaceutically acceptable salt thereof.

(4) The compound according to any one of the above (1) to (3), wherein the substituted or unsubstituted aromatic heterocyclic group is a furyl group or a thienyl group; or a pharmaceutically acceptable salt thereof.

(5) The compound according to the above (4), which is represented by formula (II):

[Formula 4]

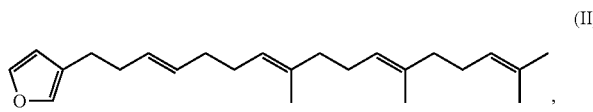

formula (VI):

[Formula 6]

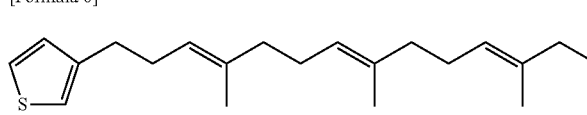

formula (CI):

[Formula 7]

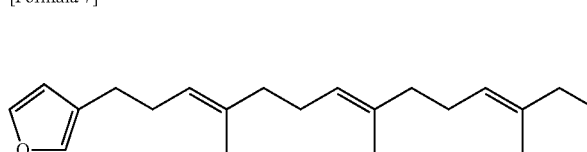

a pharmaceutically acceptable salt thereof.

(6) A pharmaceutical composition comprising the compound according to any one of the above (1) to (5) or a pharmaceutically acceptable salt thereof, and a pharmaceutically acceptable carrier.

(7) An inhibitor of insulin-like growth factor 2 expression, comprising the compound according to any one of the above (1) to (5) or a pharmaceutically acceptable salt thereof as an active ingredient.

(8) A selective inhibitor of hypoxic cell growth, comprising the compound according to any one of the above (1) to (5) or a pharmaceutically acceptable salt thereof as an active ingredient.

(9) A medicament for cancer prevention or treatment, comprising the compound according to any one of the above (1) to (5) or a pharmaceutically acceptable salt thereof as an active ingredient.

(10) The medicament according to the above (9), which is usable in combination with a chemotherapeutic drug, an immunotherapeutic drug or a hormone therapy drug.

(11) The medicament according to the above (9), which is usable in combination with radiotherapy.

(12) A method for cancer prevention or treatment, the method comprising administering, to a mammal, an effective amount of the compound according to any one of the above (1) to (5) or a pharmaceutically acceptable salt thereof.

(13) Use of the compound according to any one of the above (1) to (5) or a pharmaceutically acceptable salt thereof for production of a medicament for cancer prevention or treatment.

(14) The compound according to any one of the above (1) to (5) or a pharmaceutically acceptable salt thereof for use for cancer prevention or treatment.

Advantageous Effects of Invention

The compound represented by the general formula (C) or (I) of the present invention or a pharmaceutically acceptable salt thereof can be provided as a medicament which is clinically useful for cancer prevention or treatment in that the formula (III):

[Formula 5]

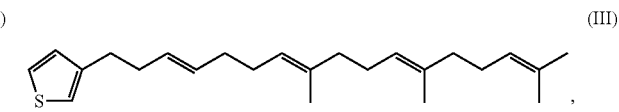

or

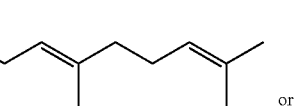

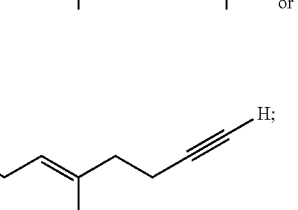

edicament has selective inhibitory activity on hypoxic cell growth in a broad range from low to high concentrations and is less toxic to normal cells.

DESCRIPTION OF EMBODIMENTS

Figure 1:
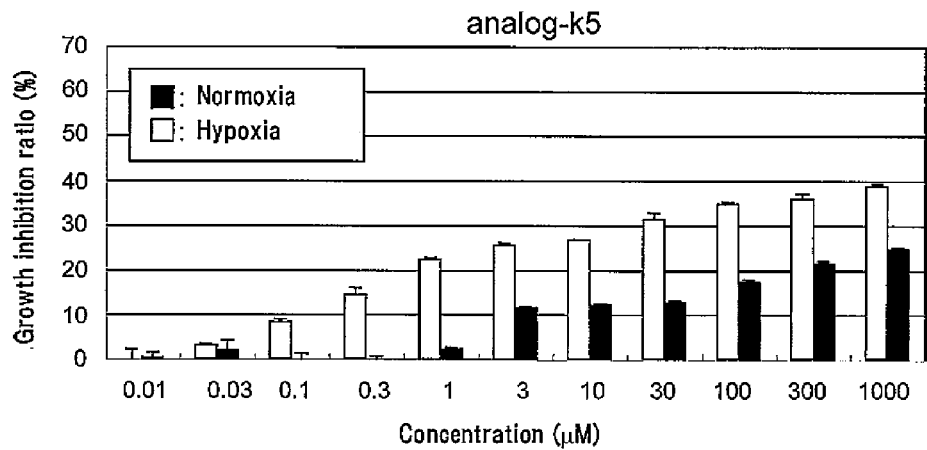
FIG. 1 shows the evaluation results of the compound represented by formula (II) (analog-k5) regarding the selective inhibitory activity on hypoxic cancer cell growth.

The present invention provides a compound represented by the general formula (C):

[Formula 8]

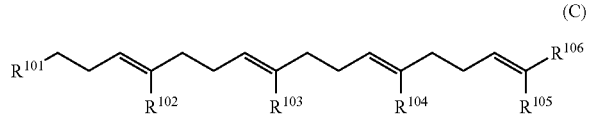

(C)

(wherein $R^{101}$ represents a substituted or unsubstituted aromatic heterocyclic group, $R^{102}$, $R^{103}$, $R^{104}$ and $R^{105}$ may be the same or different, and each represents a hydrogen atom, a halogen atom, an alkyl group having 1 to 3 carbon atoms, or a haloalkyl group having 1 to 3 carbon atoms, and $R^{106}$ represents a hydrogen atom, or a saturated or unsaturated hydrocarbon group which is a straight or branched chain having 1 to 12 carbon atoms, but excluded is the case where $R^{101}$ is a 3-furyl group, $R^{102}$, $R^{103}$, $R^{104}$ and $R^{105}$ are all methyl groups, and $R^{106}$ is a methyl group, a 4-methyl-3-pentenyl group or a 4,8-dimethyl-3,7-nonadienyl group); or a pharmaceutically acceptable salt thereof.

The present invention also provides a compound represented by the general formula (I):

[Formula 9]

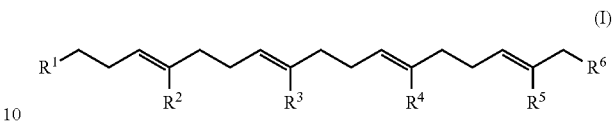

(I)

(wherein $R^1$ represents a substituted or unsubstituted aromatic heterocyclic group, $R^2$, $R^3$, $R^4$ and $R^5$ may be the same or different, and each represents a hydrogen atom, a halogen atom, an alkyl group having 1 to 3 carbon atoms, or a haloalkyl group having 1 to 3 carbon atoms, and $R^6$ represents a hydrogen atom or a prenyl group, but excluded is the case where $R^1$ is a 3-furyl group, and $R^2$, $R^3$, $R^4$ and $R^5$ are all methyl groups); or a pharmaceutically acceptable salt thereof.

The "halogen atom" refers to a fluorine atom, a chlorine atom, a bromine atom or an iodine atom.

The "alkyl group having 1 to 3 carbon atoms" refers to a methyl group, an ethyl group, a propyl group or an isopropyl group.

The "haloalkyl group having 1 to 3 carbon atoms" refers to a halogen-substituted alkyl group having 1 to 3 carbon atoms wherein the halogen atom and the alkyl group having 1 to 3 carbon atoms are as described above. Examples of the haloalkyl group having 1 to 3 carbon atoms include a chloromethyl group, a bromomethyl group, a fluoromethyl group, a trifluoromethyl group, a trichloromethyl group, a tribromomethyl group, a trichloroethyl group and a pentafluoropropyl group.

The "substituted or unsubstituted aromatic heterocyclic group" refers to a 5- or 6-membered ring group which contains, as a ring atom, at least one heteroatom such as a nitrogen atom, a sulfur atom and an oxygen atom, is optionally condensed with a benzene ring and optionally has one or more substituents selected from various kinds of groups on the ring atom. Examples of the substituted or unsubstituted aromatic heterocyclic group include pyridyl, furyl, thienyl, indolyl, quinolyl, isoquinolyl, benzofuranyl, benzothienyl, imidazolyl, benzimidazolyl, thiazolyl, oxazolyl, pyrazolyl, pyrimidyl, pyrazinyl, isoxazolyl, isoindolyl and pyrrolyl. Preferred is furyl or thienyl, and more preferred is 3-furyl or 3-thienyl.

Examples of the substituent include a fluorine atom, a chlorine atom, a cyano group, a hydroxyl group, a nitro group, an alkyl group, a cycloalkyl group, an alkoxy group, an amino group, a phenyl group, a naphthyl group, an anthryl group, a styryl group, a pyridyl group, a pyridoindolyl group, a quinolyl group and a benzothiazolyl group. These substituents may also be substituted.

The "saturated or unsaturated hydrocarbon group which is a straight or branched chain having 1 to 12 carbon atoms" include a methyl group, an ethyl group, a n-propyl group, an isopropyl group, a n-butyl group, an isobutyl group, a n-pentyl group, an isopentyl group, a neopentyl group, a 4-methylpentyl group, a vinyl group, a 1-propenyl group, a 2-propenyl group, a 2-methyl-1-propenyl group, a Z-2-butenyl group, an E-2-butenyl group, a prenyl group, a 4-methyl-3-pentenyl group, an ethynyl group, a 1-propynyl group, a 2-propynyl group, a 2-butynyl group, a 3-butynyl group, a 4-pentynyl group, a 4-hexynyl group, a 3-pentenyl group, a 4-methyl-3-hexenyl group, a 4-methyl-3-heptenyl group, a 4-methyl-3-octenyl group, a 4,6-dimethyl-3-heptenyl group, a 4,7-dimethyl-3-octenyl group, a 4,6-dimethyl-3,5-heptadienyl group, a 4,7-dimethyl-3,6-octadienyl group, a 4-methyl-3,6-heptadienyl group, a 4-methyl-3,6-octadienyl group, a 4-methyl-3,7-octadienyl group, a 4-methyloct-3-en-7-ynyl group, a 4-methylhept-3-en-6-ynyl group and a 4,8-dimethyl-3,7-nonadienyl group. Preferred is a methyl group, an ethyl group, a n-propyl group, a vinyl group, a 1-propenyl group, a prenyl group, a 4-methyl-3-pentenyl group, an ethynyl group, a 1-propynyl group, a 2-propynyl group, a 2-butynyl group, a 3-butynyl group, a 4-pentynyl group, a 4-methyloct-3-en-7-ynyl group, a 4-methylhept-3-en-6-ynyl group or a 4,8-dimethyl-3,7-nonadienyl group, and more preferred is a methyl group, a 4-methyl-3-pentenyl group or a 3-butynyl group.

Examples of the compound represented by the general formula (C) or (I) of the present invention include the following compounds (II) to (XXVII) and compounds (CI) to (CLXXI).

[Formula 10]

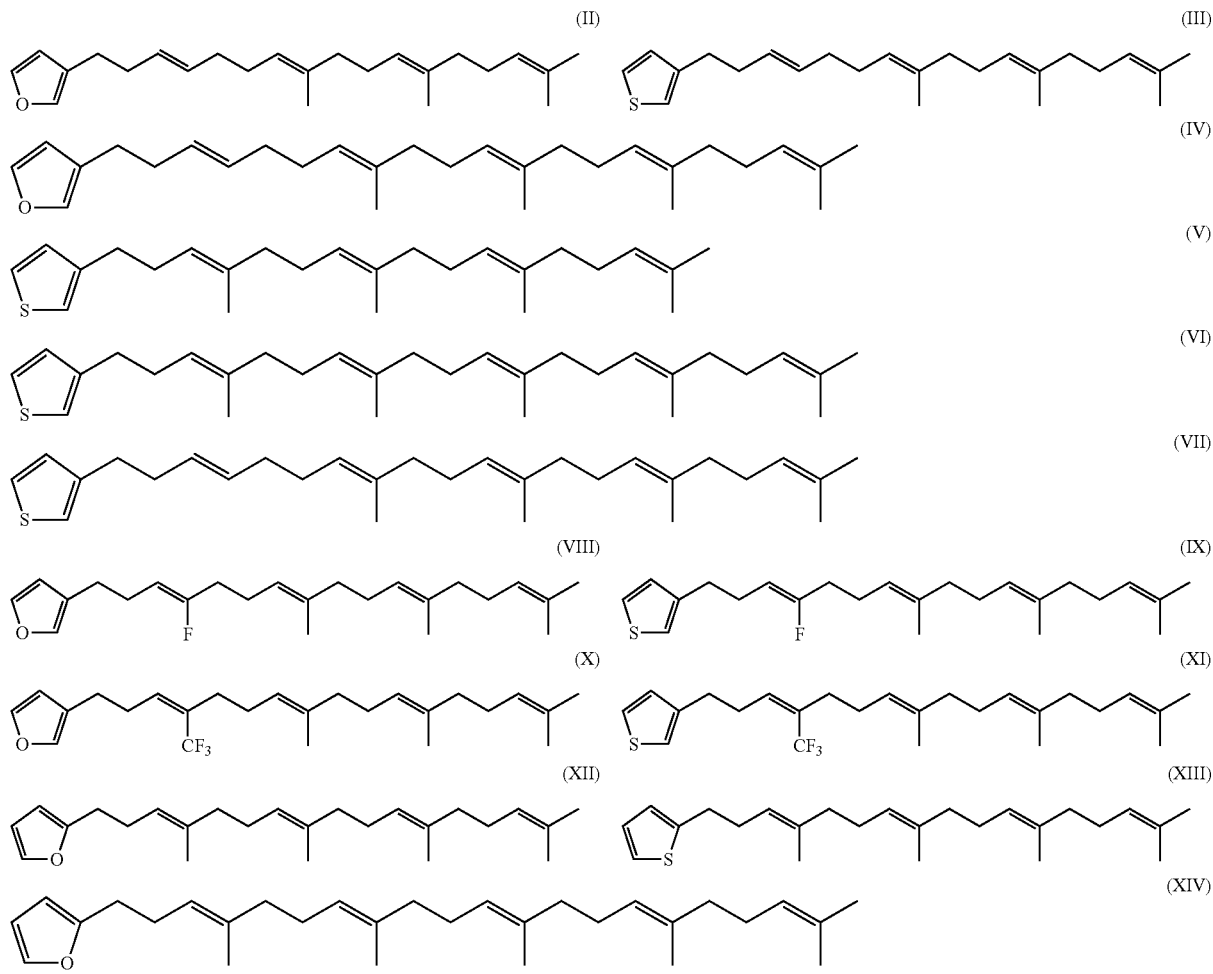

[Formula 11]

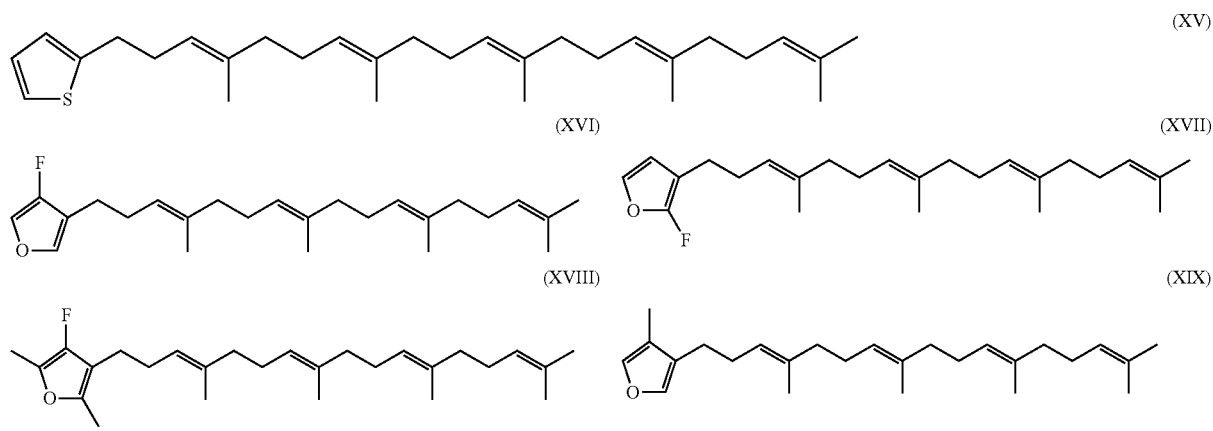

-continued
(XX)
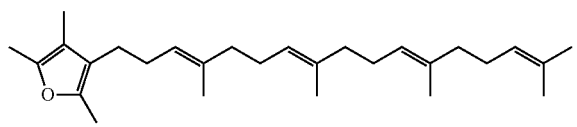
(XXI)
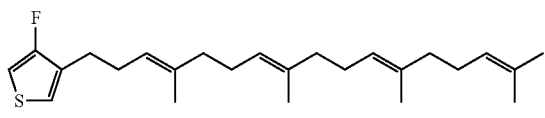
(XXII)
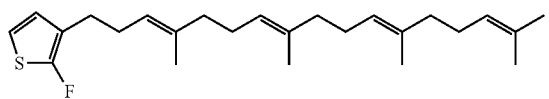
(XXIII)
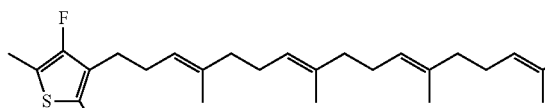
(XXIV)
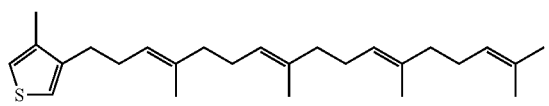
(XXV)
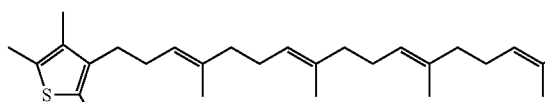
(XXVI)
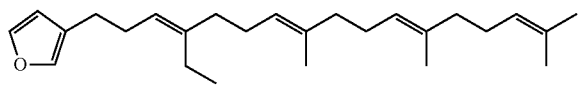
(XXVII)
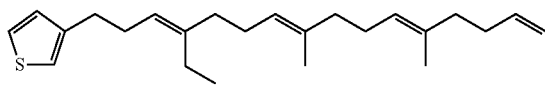
[Formula 12]
(CI)
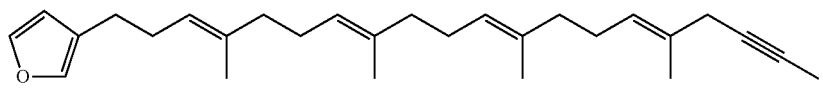
(CII)
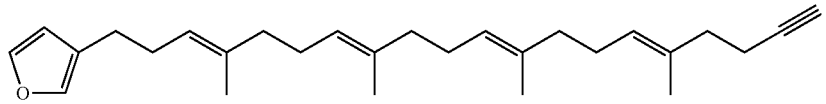
(CIII)
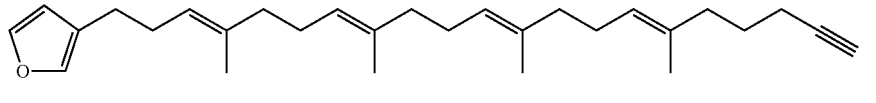
(CIV)
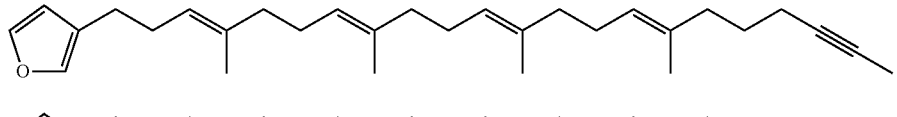
(CV)
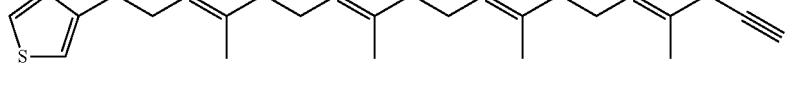
(CVI)
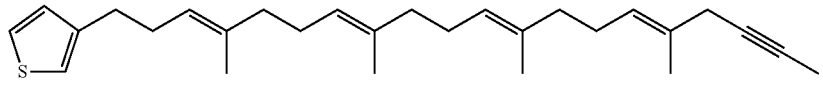
(CVII)
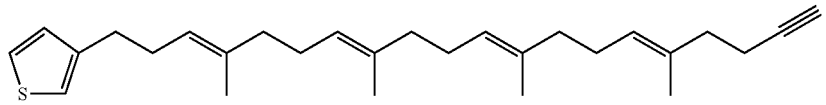
(CVIII)
(CIX)

(CX)
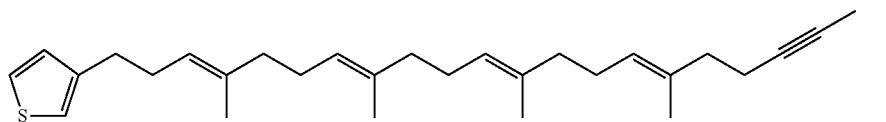
(CXI)
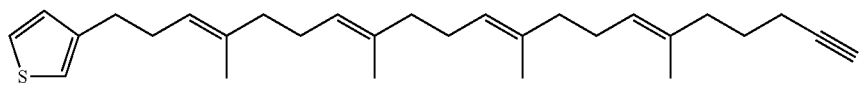
(CXII)
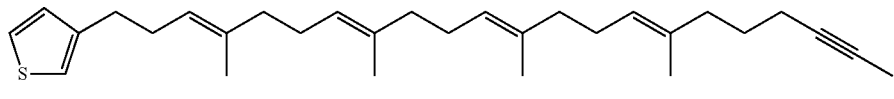
(CXIII)
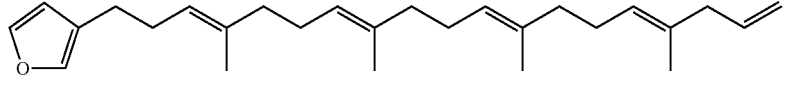
(CXIV)
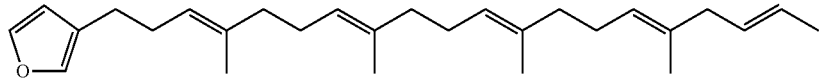
[Formula 13]
(CXV)
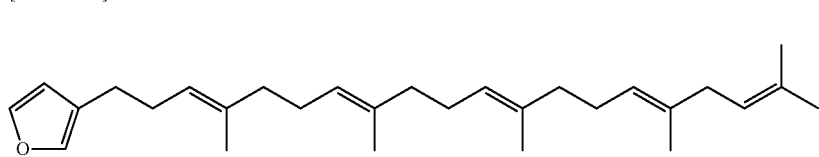
(CXVI) (CXVII)
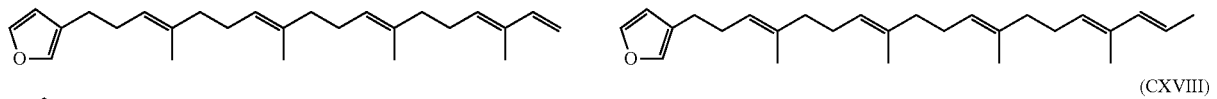
(CXVIII)
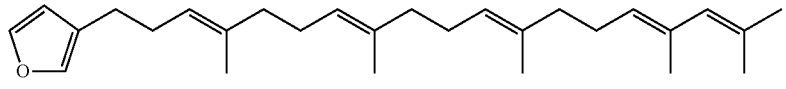
(CXIX)
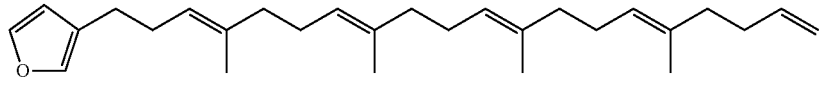
(CXX)
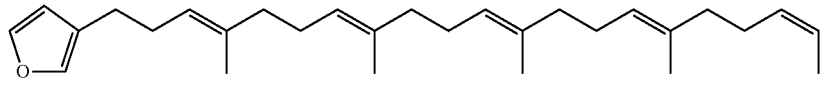
(CXXI)
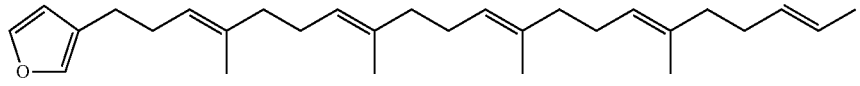
(CXXII)
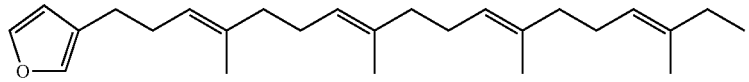
(CXXIII)
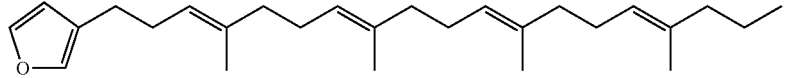
(CXXIV)
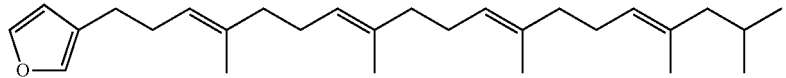
(CXXV)
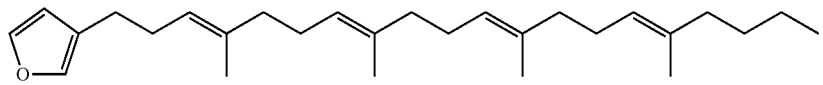

-continued
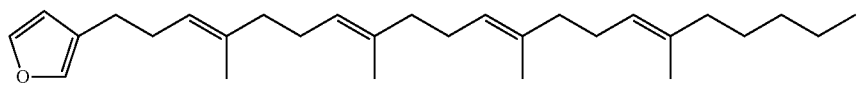 (CXXVI)
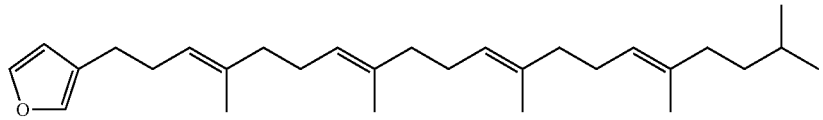 (CXXVII)
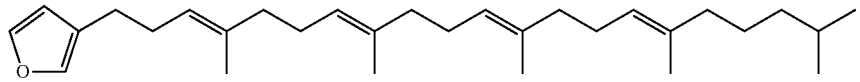 (CXXVIII)
[Formula 14]
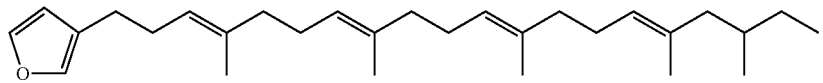 (CXXIX)
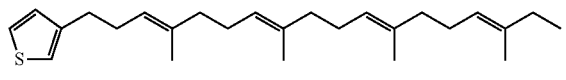 (CXXX) 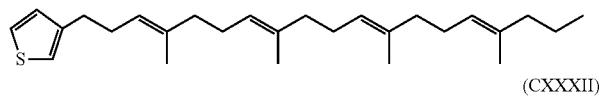 (CXXXI)
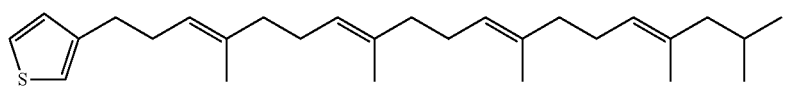 (CXXXII)
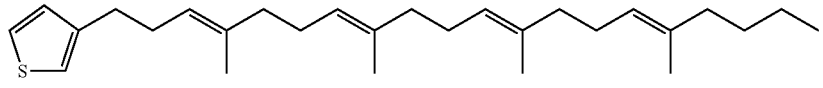 (CXXXIII)
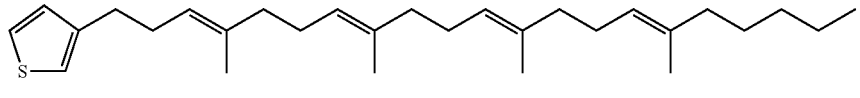 (CXXXIV)
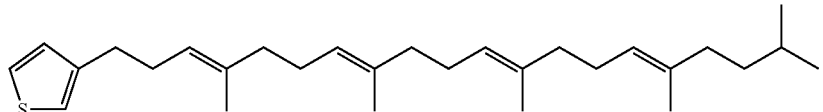 (CXXXV)
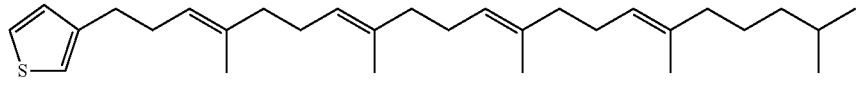 (CXXXVI)
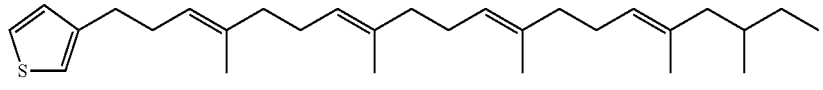 (CXXXVII)
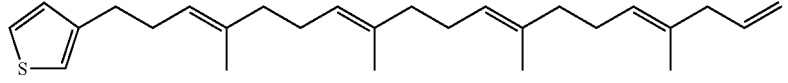 (CXXXVIII)
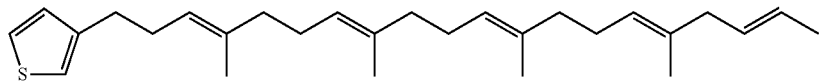 (CXXXIX)
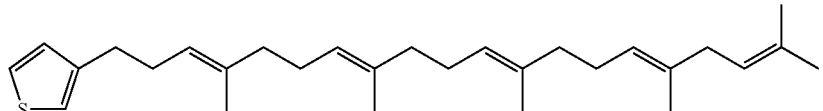 (CXL)
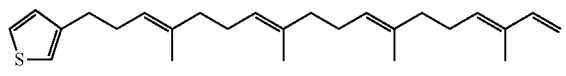 (CXLI) 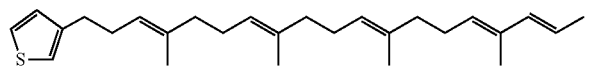 (CXLII)

-continued
[Formula 15]
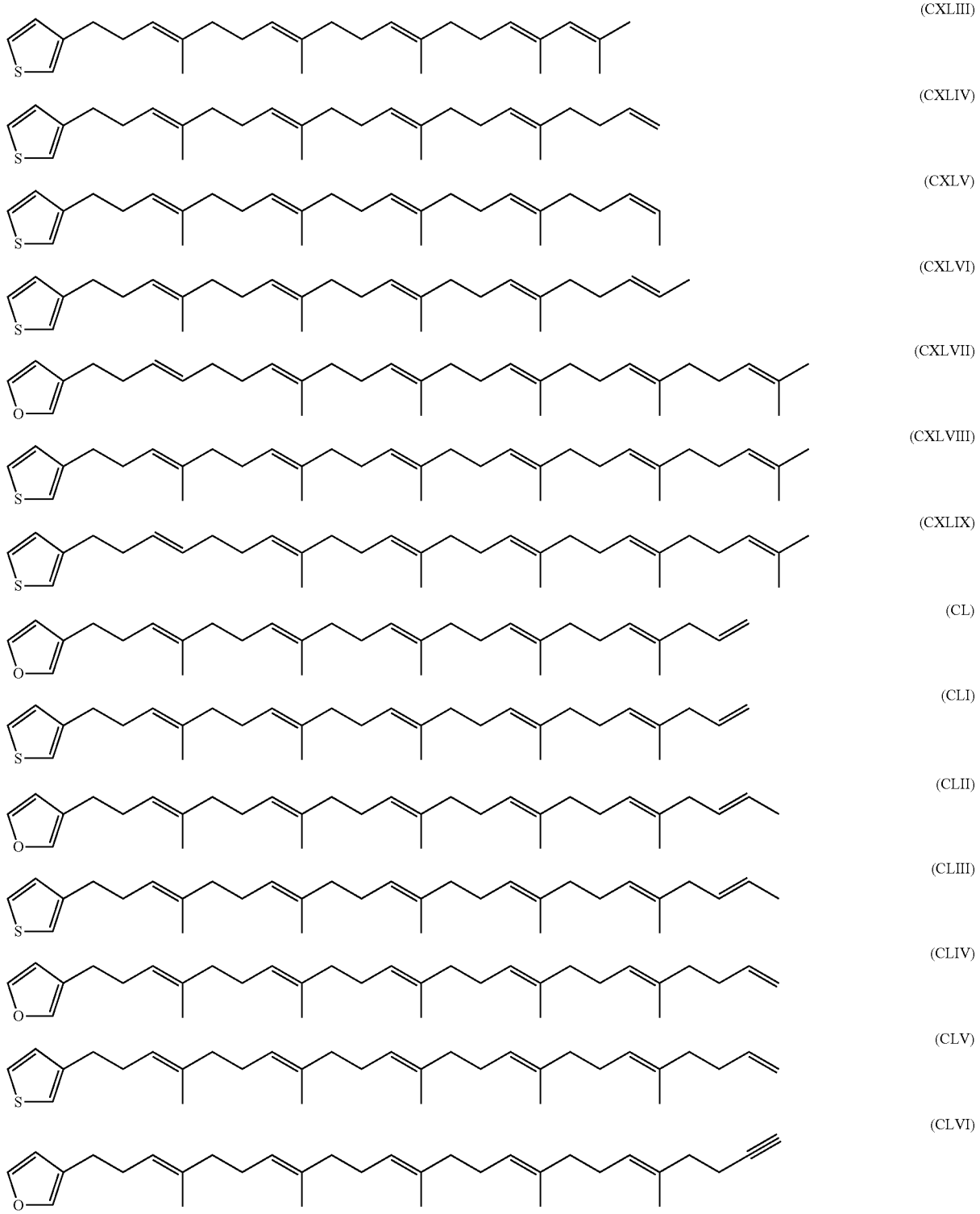
[Formula 16]
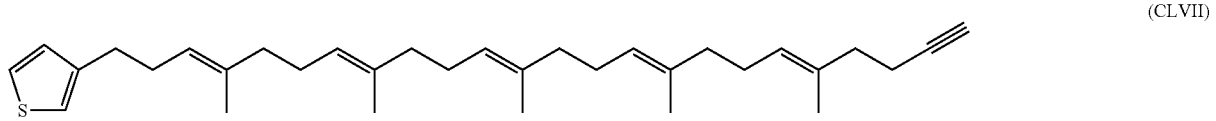

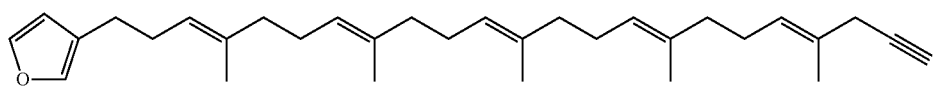 (CLVIII)
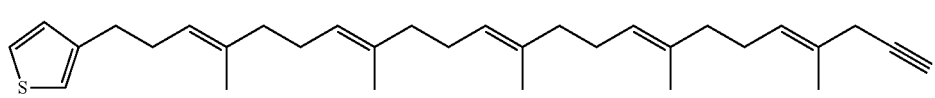 (CLIX)
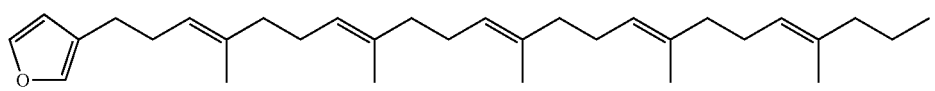 (CLX)
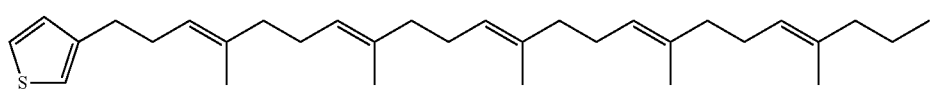 (CLXI)
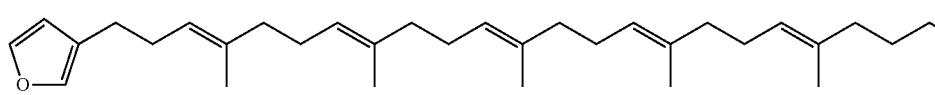 (CLXII)
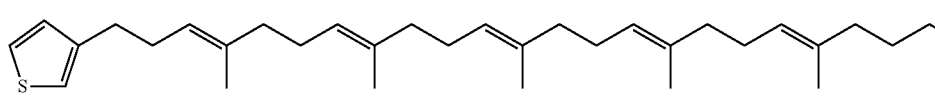 (CLXIII)
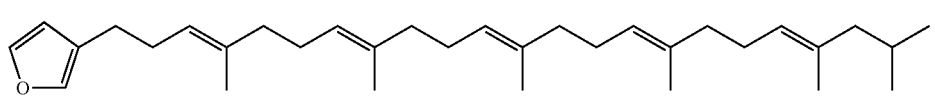 (CLXIV)
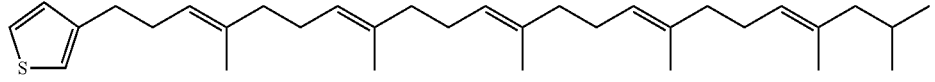 (CLXV)
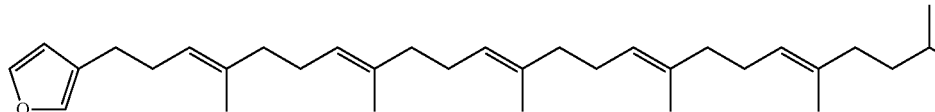 (CLXVI)
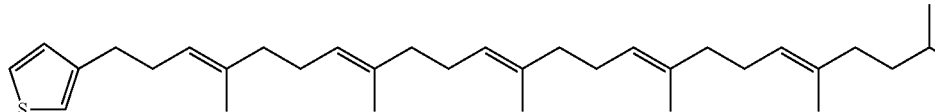 (CLXVII)
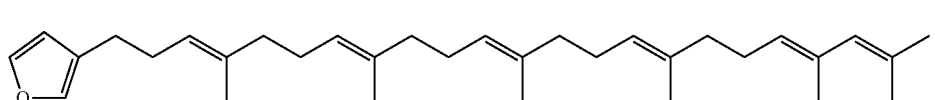 (CLXVIII)
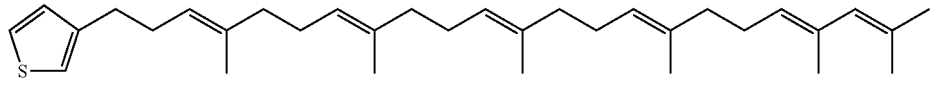 (CLXIX)
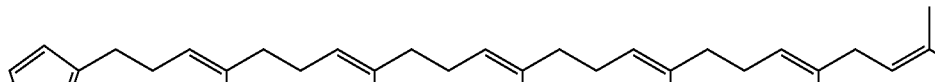 (CLXX)
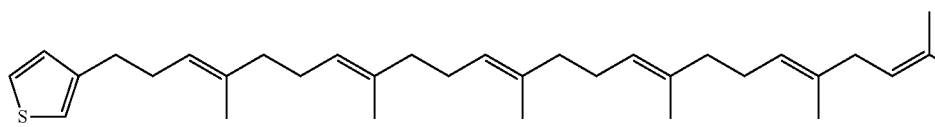 (CLXXI)

Inter alia, preferred is a compound of the general formula (C) wherein $R^{106}$ is a methyl group, a 4-methyl-3-pentenyl group or a 3-butynyl group, or a compound of the general formula (I) wherein $R^6$ is a hydrogen atom or a prenyl group.

Particularly preferred as the compound of the present invention is a compound represented by the following formula (II), (III), (VI) or (CI).

[Formula 17]

[Formula 18]

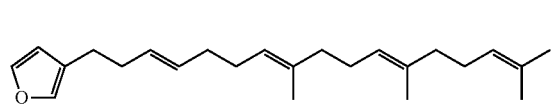

(II)

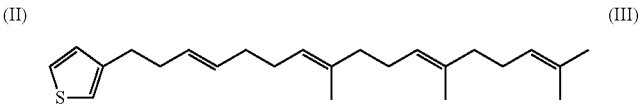

(III)

[Formula 19]

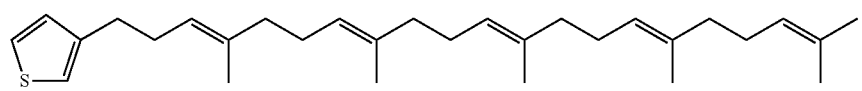

(VI)

[Formula 20]

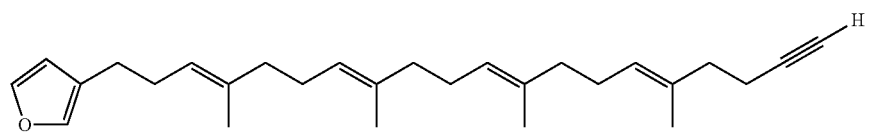

(CI)

Examples of the "pharmaceutically acceptable salt" include salts of alkali metals (for example, potassium, sodium, lithium, etc.), salts of alkaline earth metals (for example, calcium, magnesium, etc.), ammonium salts (for example, a tetramethylammonium salt, a tetrabutylammonium salt, etc.), salts of organic amines (for example, triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine), and acid addition salts (for example, inorganic acid salts, such as hydrochlorides, hydrobromides, hydriodides, sulfates, phosphates and nitrates; and organic acid salts, such as acetates, trifluoroacetates, lactates, tartrates, oxalates, fumarates, maleates, benzoates, citrates, methanesulfonates, ethanesulfonates, benzenesulfonates, toluenesulfonates, isethionates, glucuronates and gluconates).

Hereinafter, the compound represented by the general formula (C) or (I) of the present invention, or a pharmaceutically acceptable salt thereof is referred to as "the compound of the present invention."

The method for producing the compound of the present invention is not particularly limited, and the compound of the present invention can be produced according to, for example, the method described in Example 1 for synthesis of the compound represented by formula (II), the method described in Example 3 for synthesis of the compound represented by the formula (CI), the method described in Example 4 for synthesis of the compound represented by formula (VI), or the like.

Isolation and purification of the compound of the present invention can be performed by a known technique, for example, phase transfer reaction, concentration, solvent extraction, fractional distillation, pH shifting, crystallization, recrystallization, chromatography or the like. In the case where the compound of the present invention is obtained in a free form, it can be converted into an objective salt by a known technique. Conversely, in the case where the compound of the present invention is obtained in the form of a salt, it can be converted into a free form or an objective salt by a known technique.

In the case where the compound of the present invention has isomeric forms such as optical isomers, stereoisomers, regioisomers, rotamers and the like, each of the isomeric forms and mixtures thereof are included in the compound of the present invention. For example, in the case where the compound of the present invention can exist as optical isomers, each optical isomer resolved from the racemate is also included in the compound of the present invention. Each of these isomers can be individually obtained by a known synthesis method or separation method (concentration, solvent extraction, column chromatography, recrystallization, etc.).

The compound of the present invention may be a hydrate or a solvate. The compound of the present invention may be labeled with an isotope or the like.

The compound of the present invention inhibits hypoxia-inducible expression of insulin-like growth factor 2 (IGF-2) on the transcriptional level, and blocks the signal transduction pathway of IGF-1 receptor, which is a receptor of IGF-2, and thereby inhibits cell growth under hypoxia. Therefore, the present invention provides an IGF-2 expression inhibitor comprising the compound of the present invention as an active ingredient. To date, there have been no reports on compounds which inhibit IGF-2 expression on the transcriptional level. Under such circumstances, the IGF-2 expression inhibitor of the present invention is greatly useful as a reagent for research into the functions of IGF-2 and the signal transduction mechanism related thereto.

Further, the compound of the present invention inhibits hypoxia-inducible IGF-2 expression, and thereby inhibits cell growth under hypoxia more remarkably than under normoxia. Therefore, the compound of the present invention is useful as an active ingredient of a selective inhibitor of hypoxic cell growth, and can be used for cancer prevention or treatment targeting selective inhibition of hypoxic cancer cell growth. Furthermore, the compound of the present invention can be used for prevention or treatment of IGF-2-dependent diseases as well.

The cancer that the compound of the present invention can prevent or treat is not particularly limited, and examples thereof include lung cancer, colon cancer, prostate cancer, breast cancer, pancreatic cancer, esophageal cancer, gastric cancer, liver cancer, biliary tract cancer, spleen cancer, renal cancer, bladder cancer, uterine cancer, ovarian cancer, testicular cancer, thyroid cancer, brain tumor and hematological tumor. Preferred is a solid cancer in which hypoxia exists.

The present invention provides a pharmaceutical composition comprising the compound of the present invention, and a pharmaceutically acceptable carrier. The pharmaceutical composition of the present invention can be prepared by blending the compound of the present invention as an active ingredient, a pharmaceutically acceptable carrier and if needed an additive, and formulated into a dosage form. Specific examples of the dosage form include oral preparations such as tablets, coated tablets, pills, powders, granules, capsules, solutions, suspensions and emulsions; and parenteral preparations such as injections, infusions, suppositories, ointments and patches. The blending ratio of the carrier or the additive is appropriately determined based on the range of the blending ratio conventionally adopted in the pharmaceutical field. The carrier or the additive that can be blended is not particularly limited, and examples thereof include water, physiological saline and other aqueous solvents; various carriers such as aqueous bases and oily bases; and various additives such as excipients, binders, pH adjusters, disintegrants, absorption enhancers, lubricants, colorants, corrigents and fragrances.

Examples of the additive that can be blended into tablets, capsules and the like include binders such as gelatin, cornstarch, tragacanth and gum arabic; excipients such as crystalline cellulose; bulking agents such as cornstarch, gelatin and alginic acid; lubricants such as magnesium stearate; sweeteners such as sucrose, lactose and saccharin; and flavors such as peppermint, Gaultheria adenothrix oil and cherry. In the case where the unit dosage form is a capsule, a liquid carrier such as fats and oils can be further blended in addition to the above-mentioned materials. A sterile composition for injection can be prepared according to an ordinary pharmaceutical formulation practice, for example, by dissolving or suspending an active substance in a vehicle such as water for injection and a natural vegetable oil (such as sesame oil and coconut oil). As an aqueous liquid for injection, for example, physiological saline, an isotonic solution containing glucose and an auxiliary substance (for example, D-sorbitol, D-mannitol, sodium chloride, etc.), or the like can be used, optionally together with a suitable solubilizer such as alcohols (for example, ethanol), polyalcohols (for example, propylene glycol, polyethylene glycol) and nonionic surfactants (for example, polysorbate 80™, HCO-50). As an oily liquid, for example, sesame oil, soybean oil or the like can be used, optionally together with a solubilizer such as benzyl benzoate and benzyl alcohol. Further, a buffering agent (for example, a phosphate buffer, a sodium acetate buffer), a soothing agent (for example, benzalkonium chloride, procaine hydrochloride, etc.), a stabilizer (for example, human serum albumin, polyethylene glycol, etc.), a preservative (for example, benzyl alcohol, phenol, etc.), an antioxidant etc. may also be blended.

The pharmaceutical preparation that can be obtained in the above manner is safe and less toxic, and therefore can be administered to, for example, humans and other mammals (rats, mice, rabbits, sheep, pigs, cows, cats, dogs, monkeys, etc.).

The dose may vary depending on patient's state, the cancer type, the condition, the administration method and the like, but in general, the daily oral dose for a human weighing about 60 kg is, for example, about 0.1 to 1000 mg, preferably about 1.0 to 500 mg, and more preferably about 3.0 to 200 mg in terms of the active ingredient. As for the parenteral dose, the amount for one dose may vary depending on patient's state, the cancer type, the condition, the administration method and the like, but for example in the case of injections, it is usually advantageous that the active ingredient is intravenously administered in an amount of, for example, about 0.01 to 100 mg, preferably about 0.01 to 50 mg, and more preferably about 0.01 to 20 mg per kg body weight. The daily total dose may be a single dose or divided into several portions.

According to the present invention, the medicament for cancer prevention or treatment can be used in combination with another cancer therapeutic drug. Such another cancer therapeutic drug is not particularly limited, but preferred is a chemotherapeutic drug, an immunotherapeutic drug or a hormone therapy drug, for example. According to the present invention, the medicament for cancer prevention or treatment can also be used in combination with radiotherapy.

The chemotherapeutic drug is not particularly limited and examples thereof include:

alkylating agents such as nitrogen mustard, nitrogen mustard N-oxide hydrochloride, chlorambucil, cyclophosphamide, ifosfamide, thiotepa, carboquone, improsulfan tosilate, busulfan, nimustine hydrochloride, mitobronitol, melphalan, dacarbazine, ranimustine, estramustine phosphate sodium, triethylenemelamine, carmustine, lomustine, streptozocin, pipobroman, ethoglucid, carboplatin, cisplatin, miboplatin, nedaplatin, oxaliplatin, altretamine, ambamustine, dibrospidium chloride, fotemustine, prednimustine, pumitepa, Ribomustin, temozolomide, treosulfan, trofosfamide, zinostatin stimalamer, adozelesin, cystemustine and bizelesin;

antimetabolites such as mercaptopurine, 6-mercaptopurine riboside, thioinosine, methotrexate, pemetrexed, enocitabine, cytarabine, cytarabine ocfosfate, ancitabine hydrochloride, 5-FU and its derivatives (for example, fluorouracil, tegafur, UFT, doxifluridine, carmofur, galocitabine, emitefur, capecitabine, etc.), aminopterin, nelzarabine, leucovorin calcium, Tabloid, butocin, calcium folinate, calcium levofolinate, cladribine, emitefur, fludarabine, gemcitabine, hydroxycarbamide, pentostatin, piritrexim, idoxuridine, mitoguazone, tiazofurin, ambamustine and bendamustine; anticancer antibiotics such as actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride and idarubicin hydrochloride; and plant-derived anticancer drugs such as etoposide, etoposide phosphate, vinblastine sulfate, vincristine sulfate, vindesine sulfate, teniposide, paclitaxel, docetaxel and vinorelbine.

The immunotherapeutic drug is not particularly limited and examples thereof include picibanil, Krestin, sizofuran, lentinan, ubenimex, interferons, interleukins, macrophage colony-stimulating factor, granulocyte colony-stimulating factor, erythropoietin, lymphotoxins, BCG vaccine, *Coryne-* bacterium parvum, levamisole, polysaccharide K, procodazole and anti-CTLA4 antibody.

The hormone therapy drug is not particularly limited and examples thereof include fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, antiestrogens (for example, tamoxifen citrate, toremifene citrate, etc.), birth-control pills, mepitiostane, testololactone, aminoglutethimide, LH-RH agonists (for example, goserelin acetate, buserelin, leuprorelin, etc.), droloxifene, epitiostanol, ethinylestradiol sulfonate, aromatase inhibitors (for example, fadrozole hydrochloride, anastrozole, letrozole, exemestane, vorozole, formestane, etc.), antiandrogens (for example, flutamide, bicalutamide, nilutamide, etc.), 5α-reductase inhibitors (for example, finasteride, epristeride, etc.), corticosteroids (for example, dexamethasone, prednisolone, betamethasone, triamcinolone, etc.) and androgen synthesis inhibitors (for example, abiraterone, etc.).

The combined use of the medicament for cancer prevention or treatment, with another cancer therapeutic drug or radiotherapy, can provide the following effects without any limitation:
(1) synergistic effect is obtainable;
(2) the dose is reducible;
(3) prolonged treatment period is selectable; and
(4) persistent therapeutic effect can be expected.

In the case where the medicament for cancer prevention or treatment and another cancer therapeutic drug are used in combination, they may be simultaneously administered to a subject, or separately administered thereto at some interval. The dose of the drug in combined use can be determined based on its clinical dose and is appropriately selected depending on the subject, the age and body weight of the subject, the condition, the administration time, the dosage form, the administration method, the combination of drugs, etc.

EXAMPLES

Hereinafter, the present invention will be illustrated in detail by examples, but is not limited thereto.

Example 1

Synthesis of Compound Represented by Formula (II)

According to the following scheme, the compound represented by formula (II) (hereinafter referred to as "analog-k5") was synthesized.

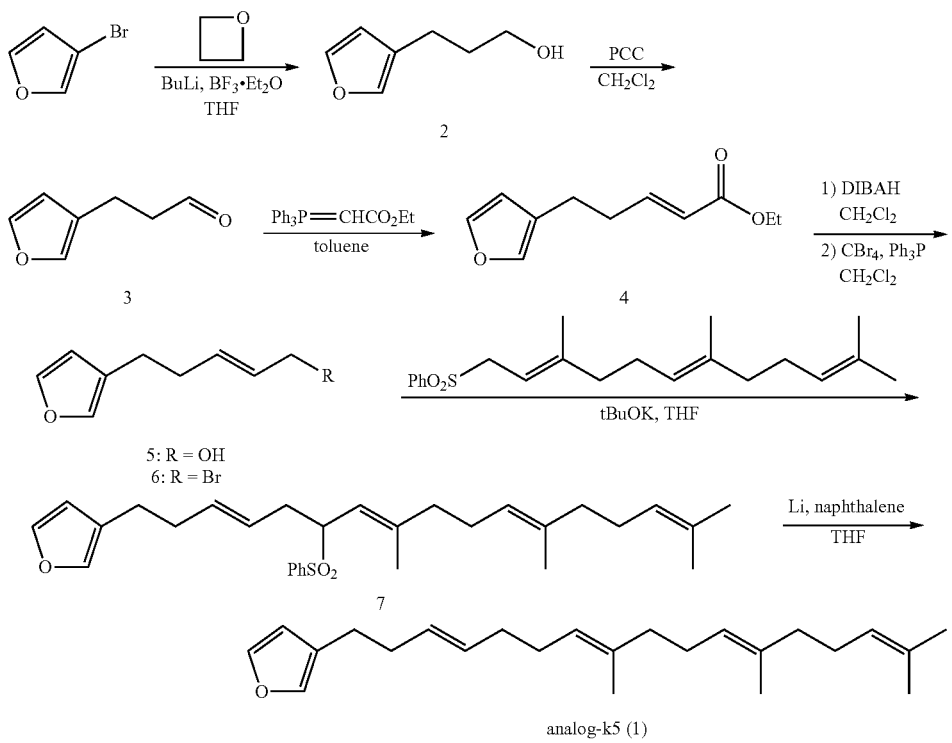

(1) Synthesis of Compound 2

To a solution of 3-bromofuran (2.94 g, 20 mmol) in THF (40 mL), n-BuLi (1.65 M in hexane, 13.3 mL, 22 mmol) was slowly added dropwise at −78° C. After 30-minute stirring, trimethylene oxide (1.57 mL, 24 mmol) was added and then $BF_3 \cdot Et_2O$ (2.72 mL, 22 mmol) was slowly added dropwise over 15 minutes. After the reaction mixture was stirred at −78° C. for 2 hours, a saturated aqueous sodium bicarbonate solution was added and then extraction with ethyl acetate was performed. The ethyl acetate layer was evaporated in vacuo and the resulting crude product was purified by silica gel column chromatography (hexane/AcOEt=3:1). Thus, compound 2 (1.41 g, 56%) was obtained as a light-yellow oily substance.

$^1$H-NMR (500 MHz, $CDCl_3$) δ: 7.36 (1H, s), 7.23 (1H, s), 6.28 (1H, s), 3.68 (2H, t, J=6.5 Hz), 2.52 (2H, t, J=7.0 Hz), 1.86-1.80 (2H, m).

(2) Synthesis of Compound 3

Pyridinium chlorochromate (3.6 g, 16.5 mmol) and Celite (4.0 g) were suspended in dichloromethane (22 mL), and a solution of compound 2 (1.41 g, 11 mmol) in dichloromethane (11 mL) was slowly added dropwise with stirring. After stirred for 3 hours, the reaction mixture was diluted with diethyl ether and then filtered through Florisil. The filtrate was evaporated in vacuo and thus compound 3 was obtained. The obtained compound was directly used for the following reaction without purification.

(3) Synthesis of Compound 4

To a solution of the above-obtained product (compound 3) in dichloromethane (10 mL), (carbethoxymethylene)triphenylphosphorane (1.80 g, 12.1 mmol) was added and the reaction mixture was stirred at room temperature for 2 hours. The reaction mixture was evaporated in vacuo and the resulting crude product was purified by silica gel column chromatography (hexane/AcOEt=10:1). Thus, compound 4 (1.39 g, 65%) was obtained as a colorless oily substance.

$^1$H-NMR (500 MHz, CDCl$_3$) δ: 7.36 (1H, s), 7.23 (1H, s), 6.98 (1H, dt, J=16.0, 6.5 Hz), 6.27 (1H, s), 5.84 (1H, dt, J=16.0, 1.5 Hz), 4.18 (2H, q, J=7.5 Hz), 2.60 (1H, t, J=7.5 Hz), 2.49-2.45 (2H, m), 1.28 (3H, t, J=7.5 Hz).

(4) Synthesis of Compound 5

To a solution of compound 4 (1.39 g, 7.2 mmol) in dichloromethane (14 mL), diisobutylaluminum hydride (DIBAH) (1.0 M in hexane, 15 mL, 15 mmol) was slowly added dropwise with stirring at 0° C. After 30-minute stirring, water (2.4 mL) and 15% NaOH (0.6 mL) were added, and the reaction mixture was stirred at room temperature for 30 minutes and then filtered through Celite. The filtrate was evaporated in vacuo and thus compound 5 was obtained. The obtained compound was directly used for the following reaction without purification.

(5) Synthesis of Compound 6

To a solution of the above-obtained product (compound 5) in dichloromethane (14 mL), CBr$_4$ (2.49 g, 7.5 mmol) and PPh$_3$ (1.97 g, 7.5 mmol) were added with stirring at 0° C. After 15-minute stirring, a saturated aqueous sodium bicarbonate solution was added and then extraction with ethyl acetate was performed. The ethyl acetate layer was evaporated in vacuo and the resulting crude product was purified by silica gel column chromatography (hexane/AcOEt=20:1). Thus, compound 6 (1.16 g, 75%) was obtained as a light-yellow oily substance.

$^1$H-NMR (500 MHz, CDCl$_3$) δ: 7.35 (1H, s), 7.22 (1H, s), 6.26 (1H, s), 5.82-5.72 (2H, m), 3.94 (2H, d, J=7.5 Hz), 2.52 (2H, t, J=8.0 Hz), 2.35-2.31 (2H, m).

(6) Synthesis of Compound 7

To a solution of compound 6 (323 mg, 1.5 mmol) and farnesyl phenylsulfone (520 mg, 1.5 mmol) in THF (3 mL), potassium t-butoxide (202 mg, 1.8 mmol) was added at −20° C. and the reaction mixture was stirred at −20° C. for 6 hours. To this, a saturated aqueous NH$_4$Cl solution was added and then extraction with ethyl acetate was performed. The ethyl acetate layer was evaporated in vacuo and the resulting crude product was purified by silica gel column chromatography (hexane/AcOEt=7:1). Thus, compound 7 (598 mg, 83%) was obtained as a light-yellow oily substance.

$^1$H-NMR (500 MHz, CDCl$_3$) δ: 7.84-7.82 (2H, m), 7.61 (1H, t, J=7.5 Hz), 7.50 (2H, t, J=7.5 Hz), 7.31 (1H, s), 7.16 (1H, s), 6.22 (1H, s), 5.53 (1H, dt, J=15.0, 7.0 Hz), 5.29 (1H, dt, J=15.0, 6.7 Hz), 5.10-5.00 (2H, m), 4.95 (1H, d, J=10.5 Hz), 3.73 (1H, td, J=10.5, 3.0 Hz), 2.88-2.84 (1H, m), 2.43 (2H, t, J=7.7 Hz), 2.38-2.19 (3H, m), 2.07-2.04 (2H, m), 1.99-1.95 (6H, m), 1.68 (3H, s), 1.59 (3H, s), 1.58 (3H, s), 1.16 (3H, s).

(7) Synthesis of Objective Compound 1 (Analog-k5)

To a solution of naphthalene (1.53 g, 12 mmol) in THF (20 mL), lithium (70 mg, 10 mmol) was added at 0° C. and the reaction mixture was stirred at 0° C. for 4 hours. The reaction mixture was cooled down to −20° C. and a solution of compound 7 (240 mg, 0.50 mmol) in THF (1.5 mL) was added dropwise with stirring. After 10-minute stirring, a saturated aqueous NH$_4$Cl solution was added and then extraction with ethyl acetate was performed. The ethyl acetate layer was evaporated in vacuo and the resulting crude product was purified by silica gel column chromatography (hexane/AcOEt=50:1). Thus, compound 1 (62 mg, 36%) was obtained as a colorless oily substance.

$^1$H-NMR (500 MHz, CDCl$_3$) δ: 7.34 (1H, s), 7.21 (1H, s), 6.27 (1H, s), 5.47-5.44 (2H, m), 5.15-5.06 (3H, m), 2.48 (2H, t, J=7.5 Hz), 2.28-2.24 (2H, m), 2.09-1.95 (12H, m), 1.68 (3H, s), 1.60 (9H, s).

$^{13}$C-NMR (125 MHz, CDCl$_3$) δ: 142.5, 138.8, 135.2, 134.9, 131.3, 130.8, 129.5, 124.8, 124.4, 124.2, 124.0, 111.1, 39.7, 33.0, 32.8, 30.3, 28.0, 26.8, 26.6, 25.7, 25.0, 17.7, 16.05, 16.00.

Example 2

Synthesis of Compound Represented by Formula (III)

The compound represented by formula (III) (hereinafter referred to as "analog-k6") was synthesized according to the method described in Example 1 for synthesis of analog-k5 except for using 3-bromothiophene instead of 3-bromofuran in (1) Synthesis of compound 2.

Example 3

Synthesis of Compound Represented by Formula (CI)

According to the following scheme, the compound represented by formula (CI) (hereinafter referred to as "analog-k13") was synthesized.

[Formula 22]

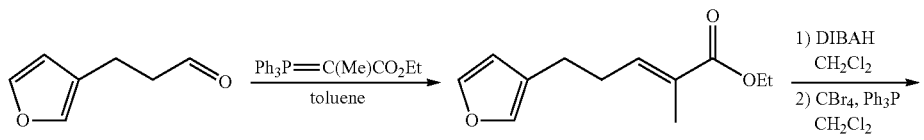

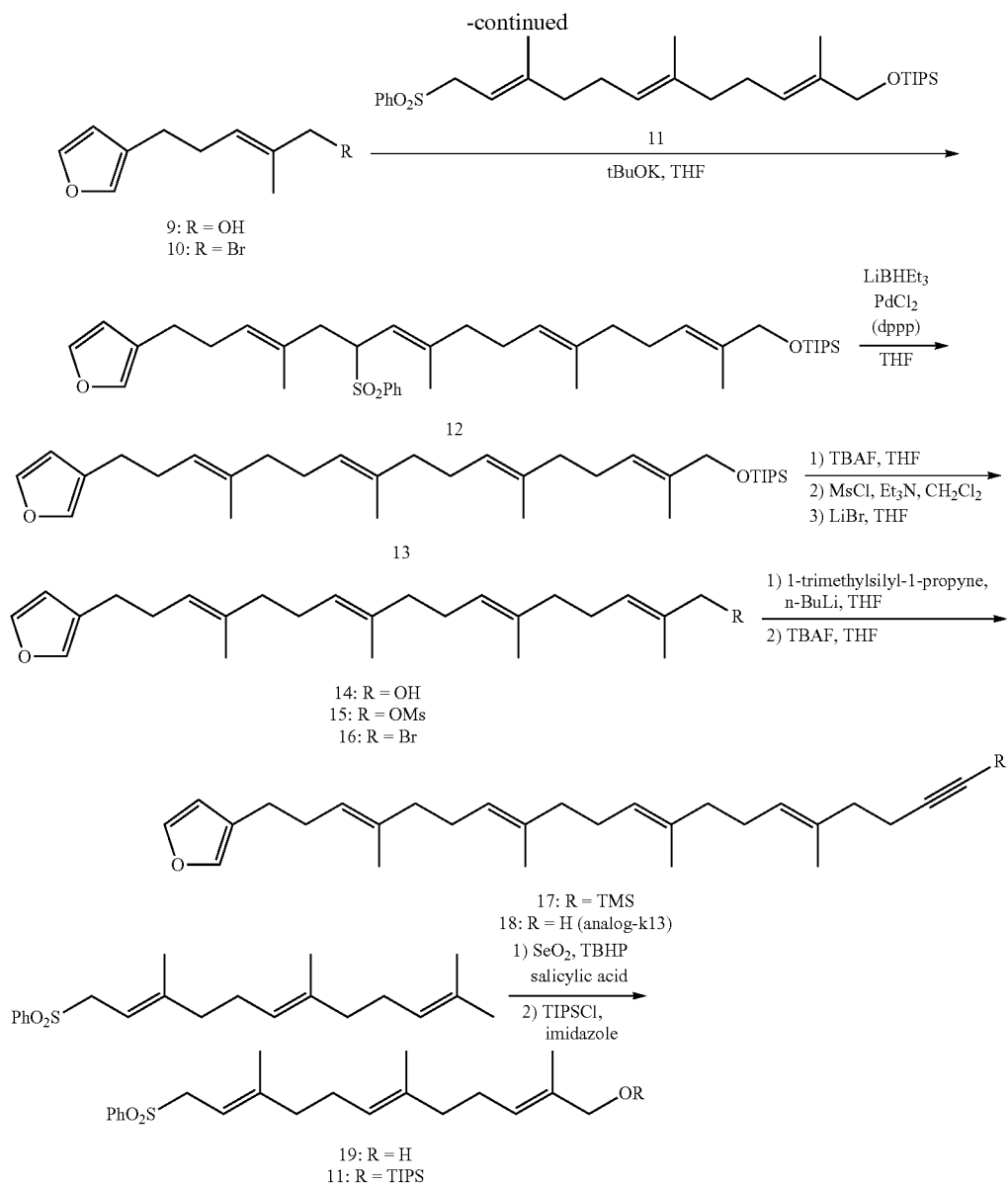

(1) Synthesis of Compound 8

To a toluene solution (16 mL) of compound 3 (198 mg, 1.59 mmol), Ph$_3$P=C(Me)CO$_2$Et (665 mg, 1.91 mmol) was added and the reaction mixture was stirred at 60° C. for 8 hours. After the reaction mixture was concentrated in vacuo, the residue was purified by silica gel column chromatography (n-hexane:AcOEt=5:1). Thus, compound 8 (247 mg, 80%) was obtained as a colorless oily substance.

$^1$H-NMR (500 MHz, CDCl$_3$) δ: 7.35 (1H, dd, J=2.4, 1.2 Hz), 7.23 (1H, d, J=1.8 Hz), 6.79-6.75 (1H, m), 6.28 (1H, s), 4.19 (2H, q, J=7.1 Hz), 2.57 (2H, t, J=7.3 Hz), 2.43 (2H, q, J=7.5 Hz), 1.81 (3H, s), 1.29 (3H, t, J=7.3 Hz).

(2) Synthesis of Compound 9

To a dichloromethane solution (1.0 mL) of compound 8 (96 mg, 0.46 mmol), DIBAH (1.0 M in n-hexane, 1.6 mL, 1.62 mmol) was added at 0° C. and the reaction mixture was stirred for 20 minutes. To this, 5% HCl was added and then extraction with dichloromethane was performed. The organic layer was dried over Na$_2$SO$_4$ and filtered and the filtrate was concentrated in vacuo. The residue was purified by silica gel column chromatography (n-hexane:AcOEt=5:1) and thus compound 9 (77 mg, quant.) was obtained as a colorless oily substance.

$^1$H-NMR (500 MHz, CDCl$_3$) δ: 7.35 (1H, s), 7.22 (1H, s), 6.28 (1H, s), 5.45 (1H, td, J=7.0, 1.4 Hz), 4.00 (2H, s), 2.49 (2H, t, J=7.6 Hz), 2.30 (2H, q, J=7.5 Hz), 1.66 (3H, s).

(3) Synthesis of Compound 10

To a dichloromethane solution (2.3 mL) of compound 9 (78 mg, 0.46 mmol), PPh$_3$ (147 mg, 0.55 mmol) and CBr$_4$ (186 mg, 0.55 mmol) were added at 0° C. and the reaction mixture was stirred for 30 minutes. To this, water was added and then extraction with dichloromethane was performed. The organic layer was dried over Na$_2$SO$_4$ and filtered and the filtrate was concentrated in vacuo. The residue was purified by silica gel column chromatography (n-hexane:AcOEt=30:1) and thus compound 10 (97 mg, quant.) was obtained as a colorless oily substance.

¹H-NMR (500 MHz, CDCl₃) δ: 7.35 (1H, s), 7.21 (1H, s), 6.27 (1H, s), 5.63 (1H, td, J=7.0, 1.0 Hz), 3.97 (2H, s), 2.49 (2H, t, J=7.6 Hz), 2.29 (2H, q, J=7.3 Hz), 1.74 (3H, s).

(4) Synthesis of Compound 12

To a THF solution (0.75 mL) of compound 10 (35 mg, 0.15 mmol) and compound 11 (70 mg, 0.14 mmol), t-BuOK (1.0 M in THF, 0.18 mL, 0.18 mmol) was added at −30° C. and the reaction mixture was stirred for 1 hour. After the temperature of the reaction mixture was allowed to rise to 0° C., a saturated aqueous NH₄Cl solution was added and then extraction with Et₂O was performed. The organic layer was dried over Na₂SO₄ and filtered and the filtrate was concentrated in vacuo. The residue was purified by silica gel column chromatography (n-hexane:AcOEt=10:1) and thus compound 12 (96 mg, 95%) was obtained as a colorless oily substance.

¹H-NMR (500 MHz, CDCl₃) δ: 7.84 (2H, d, J=8.0 Hz), 7.61 (1H, t, J=7.0 Hz), 7.51 (2H, t, J=7.5 Hz), 7.31 (1H, s), 7.15 (1H, s), 6.22 (1H, s), 5.41 (1H, t, J=6.8 Hz), 5.19 (1H, t, J=7.0 Hz), 5.05 (1H, t-like), 4.90 (1H, d, J=10.5 Hz), 4.07 (2H, s), 3.88 (1H, td, J=10.5, 3.0 Hz), 2.90 (1H, d, J=13.5 Hz), 2.39 (2H, t, J=7.8 Hz), 2.29 (1H, t, J=12.5 Hz), 2.22-2.2.09 (4H, m), 2.00 (2H, t, J=7.5 Hz), 1.93-1.92 (4H, s-like), 1.59 (3H, s), 1.58 (3H, s), 1.52 (3H, 5), 1.15 (3H, s), 1.45-1.05 (21H, m).

(5) Synthesis of Compound 13

To a THF solution (1.8 mL) of compound 12 (236 mg, 0.35 mmol), Pd(dppp) Cl₂ (42 mg, 0.071 mmol) was added and then LiBHEt₃ (1.0 M in THF, 1.24 mL, 1.24 mmol) was added at 0° C. The reaction mixture was stirred for 30 minutes. To this, a saturated aqueous NaHCO₃ solution was added and then extraction with AcOEt was performed. The organic layer was dried over Na₂SO₄ and filtered and the filtrate was concentrated in vacuo. The residue was purified by silica gel column chromatography (n-hexane:AcOEt=50:1) and thus compound 13 (160 mg, 86%) was obtained as a colorless oily substance.

¹H-NMR (500 MHz, CDCl₃) δ: 7.33 (1H, s), 7.21 (1H, s), 6.27 (1H, s), 5.42 (1H, t, J=6.5 Hz), 5.17 (1H, t, J=7.0 Hz), 5.12-5.09 (2H, m), 4.07 (2H, s), 2.45 (2H, t, J=7.8 Hz), 2.24 (2H, q, J=7.0 Hz), 2.15-1.95 (12H, m), 1.60 (9H, s), 1.59 (3H, s), 1.10-1.05 (21H, m).

(6) Synthesis of Compound 14

To a THF solution (0.4 mL) of compound 13 (23 mg, 0.043 mmol), TBAF (1.0 M in THF, 0.065 mL, 0.065 mmol) was added and the reaction mixture was stirred for 3 hours. To this, a saturated aqueous NH₄Cl solution was added and then extraction with AcOEt was performed. The organic layer was dried over Na₂SO₄ and filtered and the filtrate was concentrated in vacuo. The residue was purified by silica gel column chromatography (n-hexane:AcOEt=8:1) and thus compound 14 (16 mg, 99%) was obtained as a colorless oily substance.

¹H-NMR (500 MHz, CDCl₃) δ: 7.36 (1H, s), 7.21 (1H, s), 6.28 (1H, s), 5.39 (1H, t, J=7.0 Hz), 5.17 (1H, t, J=6.8 Hz), 5.15-5.09 (2H, m), 4.00 (2H, s), 2.45 (2H, t, J=7.5 Hz), 2.25 (2H, q, J=7.5 Hz), 2.15-1.97 (12H, m), 1.67 (3H, s), 1.61 (9H, s).

(7) Synthesis of Compound 15

To a dichloromethane solution (9.4 mL) of compound 14 (349 mg, 0.94 mmol), Et₃N (0.31 mL, 2.26 mmol) and MsCl (0.09 mL, 1.13 mmol) were successively added at −40° C. and the reaction mixture was stirred for 3 hours. To this, water was added and then extraction with AcOEt was performed. The organic layer was dried over Na₂SO₄ and filtered and the filtrate was concentrated in vacuo. Thus, compound 15 was obtained. The obtained compound was directly used for the following reaction without purification.

¹H-NMR (500 MHz, CDCl₃) δ: 7.34 (1H, s), 7.21 (1H, s), 6.28 (1H, s), 5.59 (1H, t, J=7.0 Hz), 5.17 (1H, t, J=6.8 Hz), 5.11 (2H, q, J=7.0 Hz), 4.60 (2H, s), 2.98 (3H, s), 2.45 (2H, t, J=7.5 Hz), 2.24 (2H, q, J=7.5 Hz), 2.16 (2H, q, J=7.5 Hz), 2.10-1.96 (9H, m), 1.72 (3H, s), 1.60 (9H, s).

(8) Synthesis of Compound 16

To a THF solution (15 mL) of the above-obtained product, LiBr (459 mg, 4.71 mmol) was added and the reaction mixture was stirred at room temperature for 1 hour. To this, a saturated aqueous NH₄Cl solution was added and then extraction with Et₂O was performed. The organic layer was dried over Na₂SO₄ and filtered and the filtrate was concentrated in vacuo. Thus, compound 16 was obtained. The obtained compound was directly used for the following reaction without purification.

¹H-NMR (500 MHz, CDCl₃) δ: 7.34 (1H, s), 7.21 (1H, s), 6.28 (1H, s), 5.58 (1H, t, J=7.0 Hz), 5.17 (1H, t, J=6.8 Hz), 5.14-5.09 (2H, m), 3.97 (2H, s), 2.45 (2H, t, J=7.5 Hz), 2.23 (2H, q, J=7.5 Hz), 2.16-1.96 (12H, m), 1.75 (3H, s), 1.59 (9H, s).

(9) Synthesis of Compound 17

After n-BuLi (1.67 M in hexane, 1.13 mL, 1.88 mmol) was diluted with THF (3.6 mL), 1-trimethylsilyl-1-propyne (0.28 mL, 1.88 mmol) was added at −40° C. and the temperature of the reaction mixture was allowed to rise to −20° C. with stirring over 15 minutes. The reaction mixture was cooled down to −40° C. again and a THF solution (3.6 mL) of the product obtained in the above (8) was slowly added dropwise. After the reaction mixture was stirred overnight with gradual increase in temperature, a saturated aqueous NH₄Cl solution was added and then extraction with Et₂O was performed. The organic layer was dried over Na₂SO₄ and filtered and the filtrate was concentrated in vacuo. The residue was purified by silica gel column chromatography (n-hexane:AcOEt=50:1) and thus compound 17 (296 mg, 68%) was obtained as a colorless oily substance.

¹H-NMR (500 MHz, CDCl₃) δ: 7.34 (1H, s), 7.21 (1H, s), 6.28 (1H, s), 5.18-5.09 (4H, m), 2.45 (2H, t, J=7.5 Hz), 2.29 (2H, t, J=7.5 Hz), 2.25 (2H, q, J=7.5 Hz), 2.18 (2H, t, J=7.5 Hz), 2.10-1.96 (12H, m), 1.60 (12H, s), 0.14 (9H, s).

(10) Synthesis of Compound 18 (Analog-k13)

To a THF solution (6.2 mL) of compound 17 (290 mg, 0.62 mmol), TBAF (1.0 M in THF, 0.75 mL, 0.75 mmol) was added and the reaction mixture was stirred overnight. To this, a saturated aqueous NH₄Cl solution was added and then extraction with AcOEt was performed. The organic layer was dried over Na₂SO₄ and filtered and the filtrate was concentrated in vacuo. The residue was purified by silica gel column chromatography (n-hexane:toluene=10:1) and thus compound 18 (244 mg, quant.) was obtained as a colorless oily substance.

¹H-NMR (500 MHz, CDCl₃) δ: 7.33 (1H, s), 7.21 (1H, s), 6.28 (1H, s), 5.18-5.09 (4H, m), 2.45 (2H, t, J=7.5 Hz), 2.29-2.18 (6H, m), 2.10-1.96 (12H, m), 1.94 (1H, t, J=2.5 Hz), 1.60 (12H, s).

(11) Synthesis of Compound 19

To a dichloromethane solution (1.9 mL) of SeO₂ (55 mg, 0.50 mmol) and salicylic acid (68 mg, 0.50 mmol), a 70% aqueous TBHP solution (2.55 mL, 17.8 mmol) was added at 0° C. and the reaction mixture was stirred for 10 minutes. To this, a dichloromethane solution (1.9 mL) of farnesyl phenylsulfone (1.72 g, 4.95 mmol) was slowly added dropwise at 0° C. and the reaction mixture was stirred overnight at 4° C. After dilution with toluene, extraction with AcOEt was performed. The organic layer was washed successively with a saturated aqueous NaHC% solution and an aqueous Na₂S₂O₃ solution, dried over Na$_2$SO$_4$ and filtered and the filtrate was concentrated in vacuo. Thus, a crude product containing compound 19 was obtained.

To a MeOH solution (5.0 mL) of this crude product, NaBH$_4$ (105 mg, 2.48 mmol) was added at 0° C. and the reaction mixture was stirred for 2 hours. To this, a saturated aqueous NH$_4$Cl solution was added and then extraction with AcOEt was performed. The organic layer was dried over Na$_2$SO$_4$ and filtered and the filtrate was concentrated in vacuo. The residue was purified by silica gel column chromatography (n-hexane:AcOEt=2:1) and thus compound 19 (658 mg, 38%) was obtained as a colorless oily substance.

$^1$H-NMR (500 MHz, CDCl$_3$) δ: 7.87-7.85 (2H, m), 7.63 (1H, t, J=7.5 Hz), 7.55-7.50 (2H, m), 5.38 (1H, td, J=7.0, 1.5 Hz), 5.19 (1H, dd, J=8.0, 2.0 Hz), 5.06-5.04 (1H, m), 3.98 (2H, s), 3.80 (2H, d, J=8.0 Hz), 2.14-1.96 (8H, m), 1.65 (3H, s), 1.58 (3H, s), 1.31 (3H, s), 0.87 (1H, t, J=7.0 Hz).

(12) Synthesis of Compound 11

To a DMF solution (4.3 mL) of compound 19 (622 mg, 1.72 mmol), imidazole (467 mg, 6.86 mmol) and TIPSCl (1.10 mL, 5.15 mmol) were added at 0° C. and the reaction mixture was stirred overnight while the temperature was gradually increased to room temperature. To this, a saturated aqueous NH$_4$Cl solution was added and then extraction with Et$_2$O was performed. The organic layer was dried over Na$_2$SO$_4$ and filtered and the filtrate was concentrated in vacuo. The residue was purified by silica gel column chromatography (n-hexane: AcOEt=10:1) and thus compound 11 (841 mg, 98%) was obtained as a colorless oily substance.

$^1$H-NMR (500 MHz, CDCl$_3$) δ: 7.87 (2H, d, J=8.0 Hz), 7.63 (1H, t, J=7.5 Hz), 7.53 (2H, t, J=7.5 Hz), 5.41 (1H, t, J=7.0 Hz), 5.19 (1H, t, J=8.0 Hz), 5.06 (1H, brs), 4.07 (2H, s), 3.81 (2H, d, J=8.0 Hz), 2.15-1.96 (8H, m), 1.60 (3H, s), 1.59 (3H, s), 1.32 (3H, s), 1.15-1.05 (21H).

Example 4

Synthesis of Compound Represented by Formula (VI)

According to the following scheme, the compound represented by formula (VI) (hereinafter referred to as "analog-f9") was synthesized.

[Formula 23]

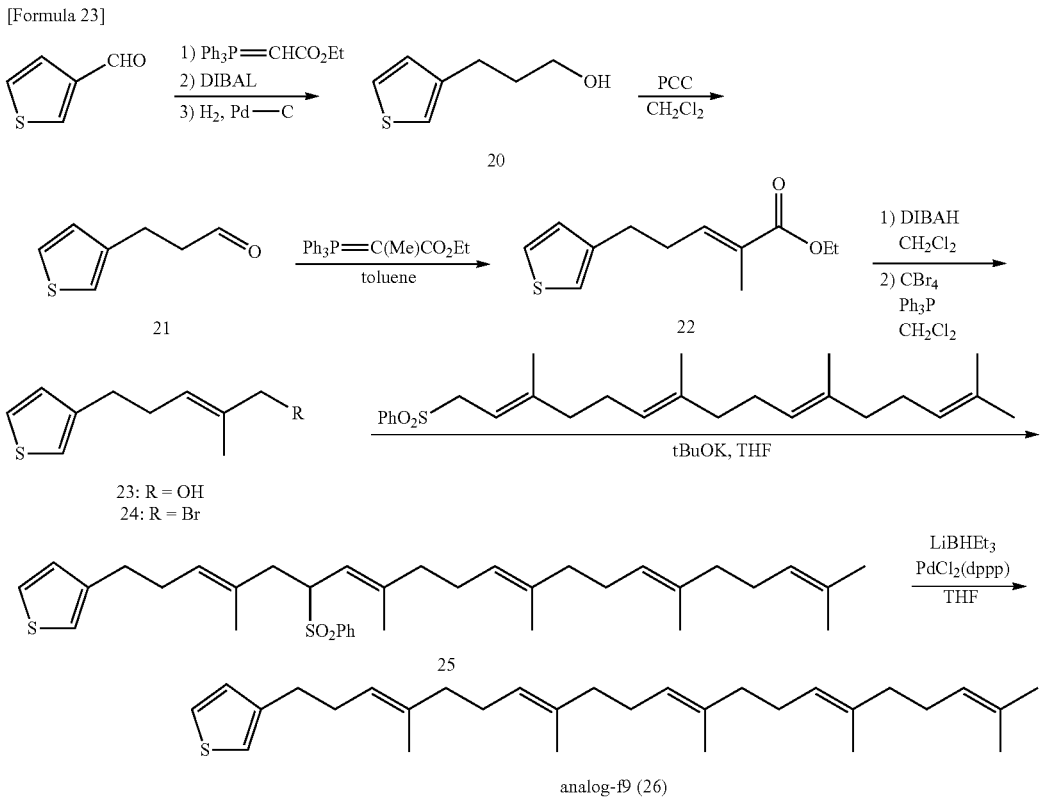

analog-f9 (26)

(1) Synthesis of Compound 20

To a dichloromethane solution (14 mL) of 3-thiophenecarboxaldehyde (313 mg, 2.79 mmol), Ph$_3$P=CHCO$_2$Et (1.17 g, 3.35 mmol) was added and the reaction mixture was stirred at room temperature for 2 hours. After the reaction mixture was concentrated in vacuo, the residue was purified by silica gel column chromatography (n-hexane:AcOEt=20:1). Thus, an ester compound (486 mg, 95%) was obtained as a colorless oily substance.

$^1$H-NMR (500 MHz, CDCl$_3$) δ: 7.67 (1H, d, J=15.9 Hz), 7.49 (1H, dd, J=2.7, 0.7 Hz), 7.32 (1H, dd, J=5.1, 2.9 Hz), 7.27 (1H, dd, J=5.1, 1.1 Hz), 6.26 (1H, d, J=15.9 Hz), 4.25 (2H, q, J=7.1 Hz), 1.33 (3H, t, J=7.1 Hz).

To a dichloromethane solution (13 mL) of the ester compound (467 mg, 2.56 mmol), DIBAH (1.0 M in n-hexane, 6.41 mL, 6.41 mmol) was added at 0° C. and the reaction mixture was stirred for 30 minutes. To this, 5% HCl was added and then extraction with dichloromethane was performed. The organic layer was dried over Na$_2$SO$_4$ and filtered and the filtrate was concentrated in vacuo. The residue was purified by silica gel column chromatography (n-hexane: AcOEt=2:1) and thus an alcohol compound (351 mg, 98%) was obtained as a colorless oily substance.

$^1$H-NMR (500 MHz, CDCl$_3$) δ: 7.21-7.19 (1H, m), 7.14 (1H, dd, J=5.2, 1.5 Hz), 7.09 (1H, d, J=3.1 Hz), 6.55 (1H, d, J=15.2 Hz), 6.15 (1H, dt, J=15.5, 5.8 Hz), (1H, m), 4.22 (2H, t, J=5.2 Hz), 1.38 (1H, brs).

To an EtOH solution (12 mL) of the alcohol compound 5 (328 mg, 2.34 mmol), Pd/C (49.8 mg) was added at room temperature and the reaction mixture was stirred under hydrogen atmosphere for 4 hours. The reaction mixture was filtered through Celite and the filtrate was concentrated in vacuo. Thus, compound 20 (336 mg, quant.) was obtained as a colorless oily substance.

$^1$H-NMR (500 MHz, CDCl$_3$) δ: 7.24 (1H, t, J=4.0 Hz), 6.94 (2H, m), 3.67 (2H, t, J=6.4 Hz), 2.72 (2H, t, J=7.6 Hz), 1.90-1.87 (2H, m), 1.25 (1H, brs).

(2) Synthesis of Compound 21

To Celite (2.47 g) and a dichloromethane solution (19 mL) of PCC (2.47 g, 11.5 mmol), compound 20 (1.36 g, 9.57 mmol) was added dropwise at room temperature and the reaction mixture was stirred for 10 hours. To this, ether was added, the reaction mixture was filtered through SiO$_2$, and the filtrate was concentrated in vacuo. The residue was purified by silica gel column chromatography (n-hexane:Et$_2$O=8:1) and thus compound 21 (900 mg, 67%) was obtained as a colorless oily substance.

$^1$H-NMR (500 MHz, CDCl$_2$) δ: 9.81 (1H, d, J=1.2 Hz), 7.25 (1H, dd, J=4.9, 3.1 Hz), 6.97 (1H, dd, J=3.1, 1.2 Hz), 6.94 (1H, dd, J=4.9, 1.2 Hz), 2.97 (2H, t, J=7.6 Hz), 2.77 (2H, td, J=7.3, 1.4 Hz).

(3) Synthesis of Compound 22

To a dichloromethane solution (1.17 mL) of compound 21 (164 mg, 1.17 mmol), Ph$_3$P=C(Me)CO$_2$Et (637 mg, 1.76 mmol) was added and the reaction mixture was stirred at room temperature for 30 minutes. After the reaction mixture was concentrated in vacuo, the residue was purified by silica gel column chromatography (n-hexane:AcOEt=20:1). Thus, compound 22 (233 mg, 89%) was obtained as a colorless oily substance.

$^1$H-NMR (500 MHz, CDCl$_3$) δ: 7.24 (1H, dd, J=4.8, 3.0 Hz), 6.93 (2H, m), 6.79-6.75 (1H, m), 4.17 (2H, q, J=7.1 Hz), 2.76 (2H, t, J=7.6 Hz), 2.48 (2H, q, J=7.5 Hz), 1.78 (3H, s), 1.27 (3H, t, J=7.0 Hz).

(4) Synthesis of Compound 23

To a dichloromethane solution (5.2 mL) of compound 22 (233 mg, 1.04 mmol), DIBAH (1.0 M in n-hexane, 2.60 mL, 2.60 mmol) was added at 0° C. and the reaction mixture was stirred for 20 minutes. To this, 5% HCl was added and then extraction with dichloromethane was performed. The organic layer was dried over Na$_2$SO$_4$ and filtered and the filtrate was concentrated in vacuo. The residue was purified by silica gel column chromatography (n-hexane:AcOEt=3:1) and thus compound 23 (175 mg, 92%) was obtained as a colorless oily substance.

$^1$H-NMR (500 MHz, CDCl$_3$) δ: 7.22 (1H, dd, J=4.9, 3.1 Hz), 6.93 (2H, m), 5.44 (1H, td, J=7.2, 1.4 Hz), 3.98 (2H, s), 2.68 (2H, t, J=7.9 Hz), 2.35 (2H, q, J=7.5 Hz), 1.62 (3H, s), 1.22 (1H, brs).

(5) Synthesis of Compound 24

To a dichloromethane solution (4.7 mL) of compound 23 (173 mg, 0.95 mmol), PPh$_3$ (323 mg, 1.23 mmol) and C3r$_4$ (409 mg, 1.23 mmol) were added at 0° C. and the reaction mixture was stirred for 15 minutes. To this, water was added and then extraction with dichloromethane was performed. The organic layer was dried over Na$_2$SO$_4$ and filtered and the filtrate was concentrated in vacuo. The residue was purified by silica gel column chromatography (n-hexane:AcOEt=30:1) and thus compound 24 (208 mg, 89%) was obtained as a colorless oily substance.

$^1$H-NMR (500 MHz, CDCl$_3$) δ: 7.26 (1H, t, J=4.0 Hz), 6.95 (2H, m), 5.65 (1H, t, J=7.0 Hz), 3.98 (2H, s), 2.72 (2H, t, J=7.3 Hz), 2.37 (2H, q, J=7.3 Hz), 1.74 (3H, s).

(6) Synthesis of Compound 25

To a THF solution (1.8 mL) of compound 24 (99 mg, 0.40 mmol) and geranylgeranyl phenylsulfone (153 mg, 0.37 mmol), t-BuOK (10 M in THF, 0.44 mL, 0.44 mmol) was added at −40° C. and the reaction mixture was stirred for 30 minutes. After the temperature of the reaction mixture was allowed to rise to 0° C., a saturated aqueous NH$_4$Cl solution was added and then extraction with AcOEt was performed. The organic layer was dried over Na$_2$SO$_4$ and filtered and the filtrate was concentrated in vacuo. The residue was purified by silica gel column chromatography (n-hexane:AcOEt=10:1) and thus compound 25 (162 mg, 76%) was obtained as a colorless oily substance.

$^1$H-NMR (500 MHz, CDCl$_3$) δ: 7.84 (2H, d, J=7.0 Hz), 7.61 (1H, t, J=7.3 Hz), 7.51 (2H, t, J=7.6 Hz), 7.21 (1H, dd, J=5.0, 3.0 Hz), 6.89-6.88 (2H, m), 5.20 (1H, t, J=7.0 Hz), 5.10-5.02 (3H, m), 4.91 (1H, d, J=10.0 Hz), 3.88 (1H, td, J=10.7, 2.9 Hz), 2.89 (1H, d, J=12.8 Hz), 2.60 (2H, t, J=7.6 Hz), 2.30-2.26 (3H, m), 2.09-1.90 (12H, m), 1.68 (3H, s), 1.60 (3H, s), 1.59 (3H, s), 1.58 (3H, s), 1.50 (3H, s), 1.15 (3H, s).

(7) Synthesis of Compound 26 (Analog-f9)

To a THF solution (1.44 mL) of compound 25 (166 mg, 0.29 mmol), Pd(dppp) Cl$_2$ (34 mg, 0.057 mmol) was added and then LiBHEt$_3$ (1.0M in THF, 1.0 mL, 1.0 mmol) was added at 0° C. The reaction mixture was stirred for 20 minutes. To this, a saturated aqueous NH$_4$Cl solution was added and then extraction with AcOEt was performed. The organic layer was dried over Na$_2$SO$_4$ and filtered and the filtrate was concentrated in vacuo. The residue was purified by silica gel column chromatography (n-hexane:AcOEt=20:1) and thus compound 26 (110 mg, 87%) was obtained as a colorless oily substance.

$^1$H-NMR (500 MHz, CDCl$_3$) δ: 7.23 (1H, dd, J=4.9, 3.1 Hz), 6.95 (1H, dd, J=4.9, 1.2 Hz), 6.93 (1H, dd, J=3.1, 1.1 Hz), 5.18 (1H, td, J=6.9, 1.0 Hz), 5.13-5.09 (4H, m), 2.66 (2H, t, J=7.6 Hz), 2.31 (2H, q, J=7.5 Hz), 2.10-1.96 (16H, m), 1.68 (3H, s), 1.61 (12H, s), 1.58 (3H, s).

Example 5

Evaluation of Selective Inhibitory Activity on Hypoxic Cancer Cell Growth (1)

Analog-k5, which is represented by formula (II), and analog-k6, which is represented by formula (III), were used as test compounds and furospinosulin-1 was used as the control compound. The test compounds and the control compound were separately dissolved in EtOH, and the respective solutions were prepared at predetermined concentrations. The cells used were human prostate cancer DU145 cells. Analog-k6 was synthesized according to the method described in Example 1 for synthesis of analog-k5 except for using 3-bromothiophene instead of 3-bromofuran.

To each well of 96-well multiwell plates, 200 μL (1×10$^4$ cells/well) of a DU145 cell suspension was added, and pre-culture was performed under conditions of 5% CO$_2$ and 37° C. for 4 hours. Then, the multiwell plates were placed in a hypoxic culture chamber (manufactured by Mitsubishi Gas Chemical Company, Inc.) of 1% O$_2$, 5% CO$_2$ and 94% N$_2$ (hypoxic conditions) and culture was performed for 12 hours.

Then, the test compound solutions in EtOH were added to the corresponding wells in a volume of 2 μL per well, and culture was further continued under hypoxic conditions for 24 hours. After 24 hours of culture, MTT (3-(4,5-dimethylthiazol-2-yl)-2,5-diphenyltetrazolium bromide) reagent prepared at 200 μg/mL was added in a volume of 50 μL per well, and culture was performed under conditions of 5% $CO_2$ and 37° C. for 3 hours. Next, after removal of the culture medium, the resulting MTT formazan was extracted with 200 μL of DMSO per well. The amount of the formazan dye was quantified by a colorimetric method (OD 560 nm) and the ratio of growth inhibition was calculated.

Meanwhile, the inhibitory activity of the test compounds on normoxic cell growth was measured in the following manner. To each well of 96-well multiwell plates, 200 μL ($1\times10^4$ cells/well) of a DU145 cell suspension was added, and culture was performed under conditions of 5% $CO_2$ and 37° C. for 12 hours. Then, the test compound solutions in EtOH were added to the corresponding wells in a volume of 2 μL per well, and culture was further continued under the same conditions for 24 hours. After 24 hours of culture, as is the case in hypoxic conditions, the MTT reagent was added and finally the ratio of growth inhibition was calculated.

Figure 2:
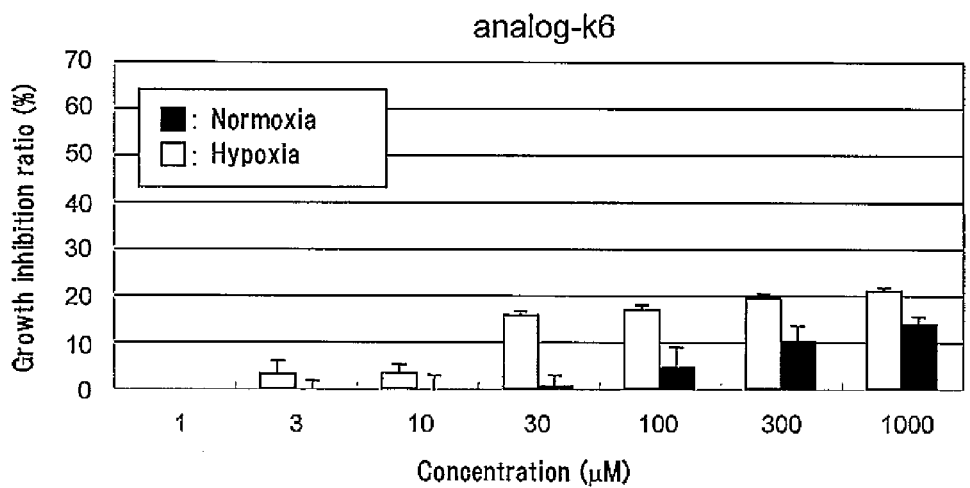
FIG. 2 shows the evaluation results of the compound represented by formula (III) (analog-k6) regarding the selective inhibitory activity on hypoxic cancer cell growth.
Figure 3:
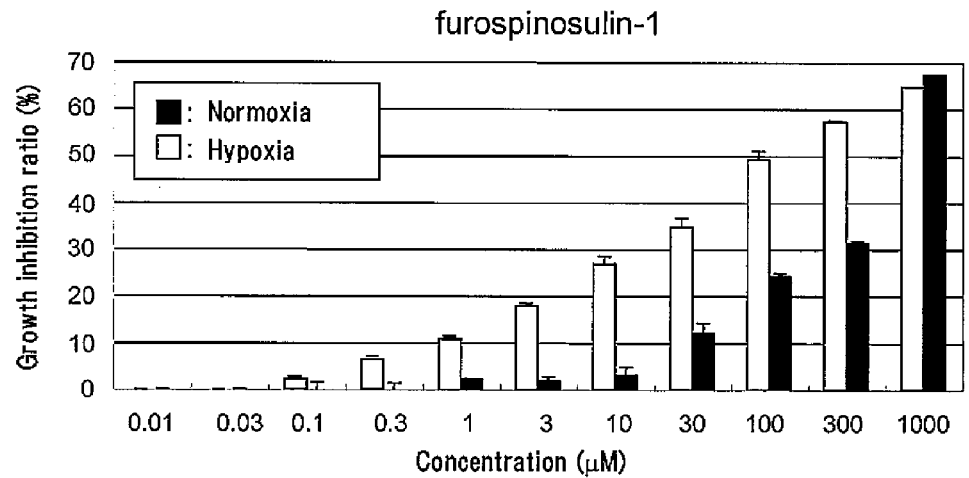
FIG. 3 shows the evaluation results of furospinosulin-1 regarding the selective inhibitory activity on hypoxic cancer cell growth.

The results are shown in FIGS. 1, 2 and 3. FIG. 1 shows the results of analog-k5, FIG. 2 shows the results of analog-k6, and FIG. 3 shows the results of furospinosulin-1. As is clear from FIG. 3, the control compound furospinosulin-1 showed selective inhibitory activity on hypoxic cell growth in the concentrations of 300 μM or lower, but at 1000 μM, furospinosulin-1 showed growth inhibitory activity even against normoxic cells. That is, it was demonstrated that the cell-growth inhibitory activity of furospinosulin-1 in a high concentration is not selective for hypoxic cells. On the other hand, as is clear from FIGS. 1 and 2, analog-k5 and analog-k6, even at 1000 μM, individually showed selective inhibitory activity on hypoxic cell growth.

From these results, it was indicated that analog-k5 and analog-k6 in a high dose individually have a lower inhibitory activity on normoxic cell growth as well as smaller side effects as compared with furospinosulin-1.

Example 6

Evaluation of Antitumor Activity in Mouse Cancer Cell Transplant Model (1)

A suspension of the test compound analog-k5 was prepared at predetermined concentrations in 1% CMC. The vehicle (1% CMC) was administered to the control group.

Mouse sarcoma S180 cells were prepared as a suspension of the density of $1\times10^7$ cells/mL in a serum-free RPMI culture medium and the suspension was kept on ice. Then, 100 μL ($1\times10^6$ cells) each of the cell suspension was subcutaneously inoculated to the ventral side in female ddY mice (5-week old, six mice/group) with an injection needle of 23G. The mice were maintained for one week for engraftment of the 5180 cells. The test compound (10 mg/kg, 25 mg/kg and 50 mg/kg) or the vehicle (1% CMC) was orally administered on a schedule of once every two days, 7 times in total. The antitumor activity was evaluated as follows: one day after the final administration, tumors were isolated and weighed and then the tumor weight was compared between the test compound administration groups and the control group. Significance analysis was performed using a Dunnett's test at a significance level of 5%.

Figure 4:
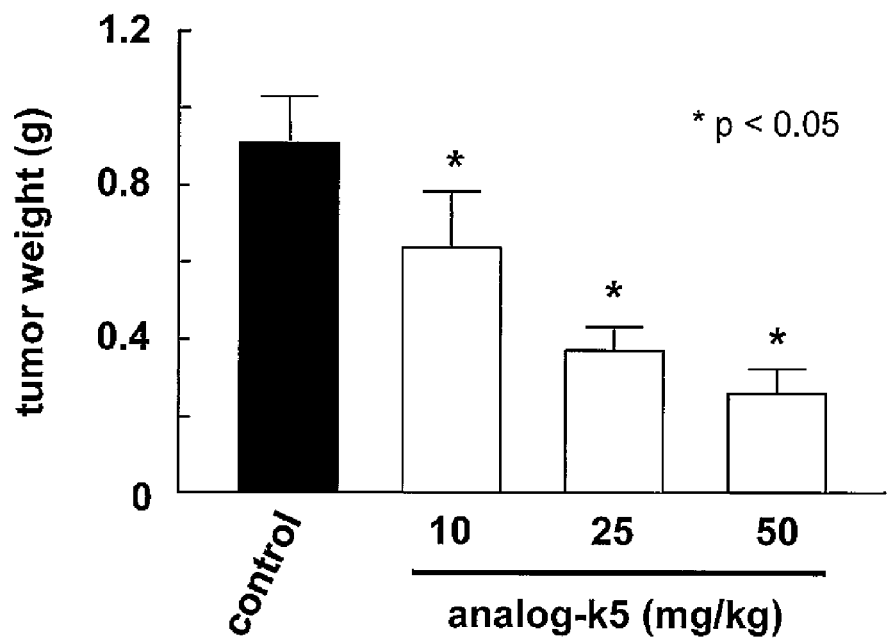
FIG. 4(a) shows the evaluation results of the compound represented by formula (II) (analog-k5) on the antitumor activity in a mouse cancer cell transplant model.
FIG. 4(b) shows a photograph of tumors isolated from a mouse cancer cell transplant model to which the compound represented by formula (II) (analog-k5) had been administered.
Figure 4:

The results are shown in FIGS. 4(a) and (b). (a) is a graph showing the tumor weight of each group, and (b) is a photograph of isolated tumors. As is clear from FIGS. 4(a) and (b), the tumor weights of the 10 mg/kg, 25 mg/kg and 50 mg/kg analog-k5 administration groups were reduced to 70%, 41% and 28% of that of control group, respectively. Thus, analog-k5 showed marked antitumor activity. In no administration groups, weight loss or diarrhea, or visual abnormalities in organs of the mice were observed.

Example 7

Evaluation of Selective Inhibitory Activity on Hypoxic Cancer Cell Growth (2)

Analog-f9, which is represented by formula (VI), and analog-k13, which is represented by formula (CI), were used as the test compounds, and both were evaluated for the selective inhibitory activity on hypoxic cancer cell growth according to the same method as described in Example 5.

Figure 5:
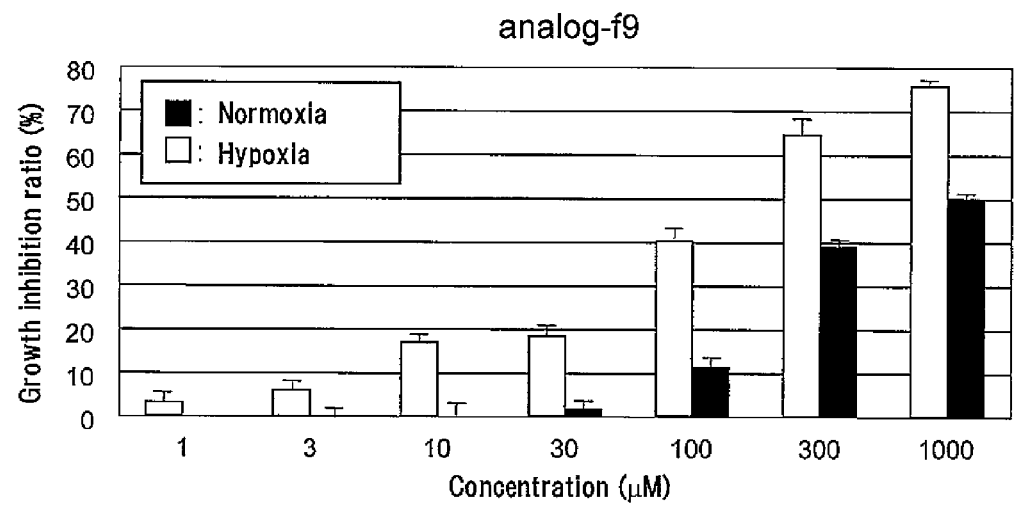
FIG. 5 shows the evaluation results of the compound represented by formula (VI) (analog-f9) regarding the selective inhibitory activity on hypoxic cancer cell growth.
Figure 6:
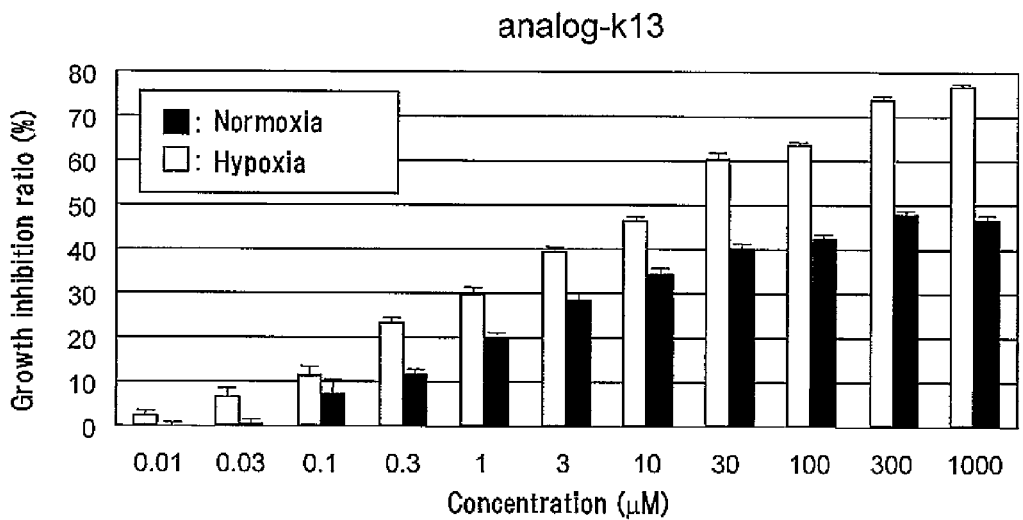
FIG. 6 shows the evaluation results of the compound represented by formula (CI) (analog-k13) regarding the selective inhibitory activity on hypoxic cancer cell growth.

The results are shown in FIGS. 5 and 6. FIG. 5 shows the results of analog-f9 and FIG. 6 shows the results of analog-k13. The results of the control compound furospinosulin-1 were similar to those in FIG. 3 and thus are not shown here. As is clear from FIGS. 5 and 6, analog-f9 and analog-k13, even at 1000 μM, individually showed selective inhibitory activity on hypoxic cell growth. Therefore, it was indicated that analog-f9 and analog-k13 in a high dose individually have a lower inhibitory activity on normoxic cell growth as well as smaller side effects as compared with furospinosulin-1. From FIG. 5, it was also found that analog-f9 has a remarkably low inhibitory activity on normoxic cell growth in the concentrations of 100 μM or lower, and hardly inhibits normoxic cell growth particularly in the concentrations of 10 μM or lower. Therefore, it was indicated that analog-f9 has few side effects in a low dose. As is clear from FIG. 6, analog-k13, in the entire range of tested concentrations, showed selective inhibition of hypoxic cell growth, which was stronger than that of furospinosulin-1. Therefore, it was indicated that analog-k13 has a stronger effect even in a lower dose as compared with furospinosulin-1.

Example 8

Evaluation of Antitumor Activity in Mouse Cancer Cell Transplant Model (2)

Analog-f9, which is represented by formula (VI), and analog-k13, which is represented by formula (CI), were used as the test compounds, and both were evaluated for the antitumor activity in a mouse cancer cell transplant model according to the same method as described in Example 6. However, the number of mice per group was changed to four, and the doses of test compounds were changed to 3 mg/kg, 10 mg/kg and 25 mg/kg.

Figure 7A:
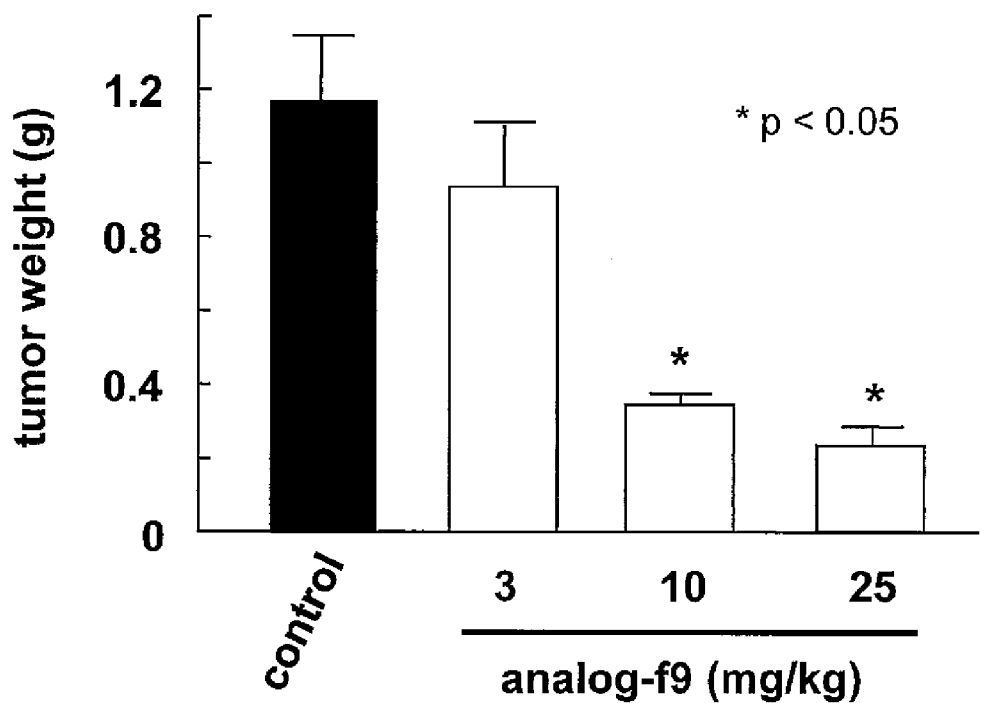
FIG. 7(a) shows the evaluation results of the compound represented by formula (VI) (analog-f9) on the antitumor activity in a mouse cancer cell transplant model.
Figure 7B:
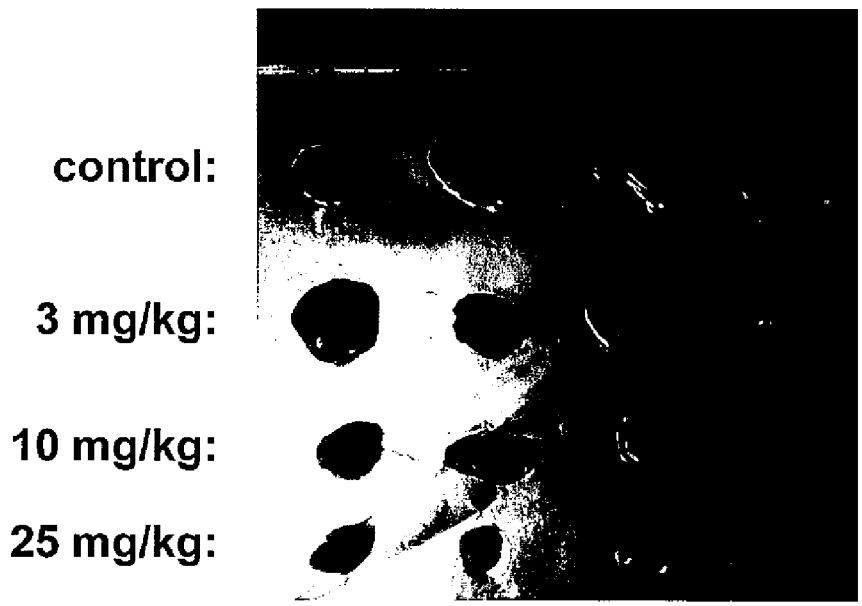
FIG. 7(b) shows a photograph of tumors isolated from a mouse cancer cell transplant model to which the compound represented by formula (VI) (analog-f9) had been administered.
Figure 8:
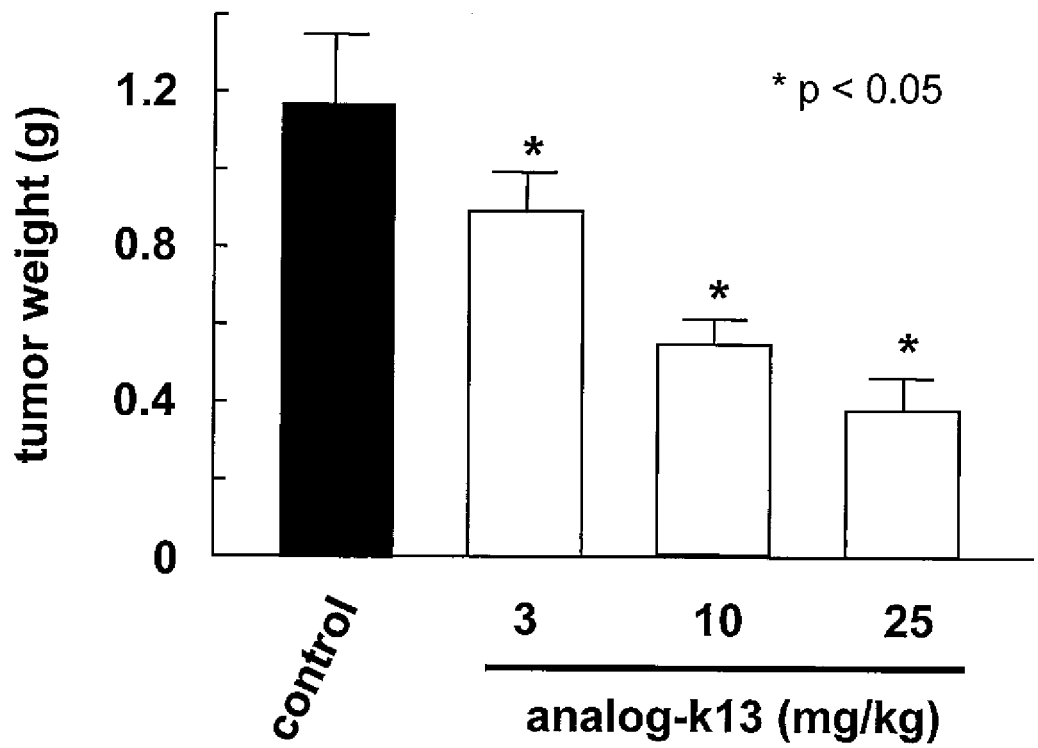
FIG. 8(a) shows the evaluation results of the compound represented by formula (CI) (analog-k13) on the antitumor activity in a mouse cancer cell transplant model.
FIG. 8(b) shows a photograph of tumors isolated from a mouse cancer cell transplant model to which the compound represented by formula (CI) (analog-k13) had been administered.
Figure 8:
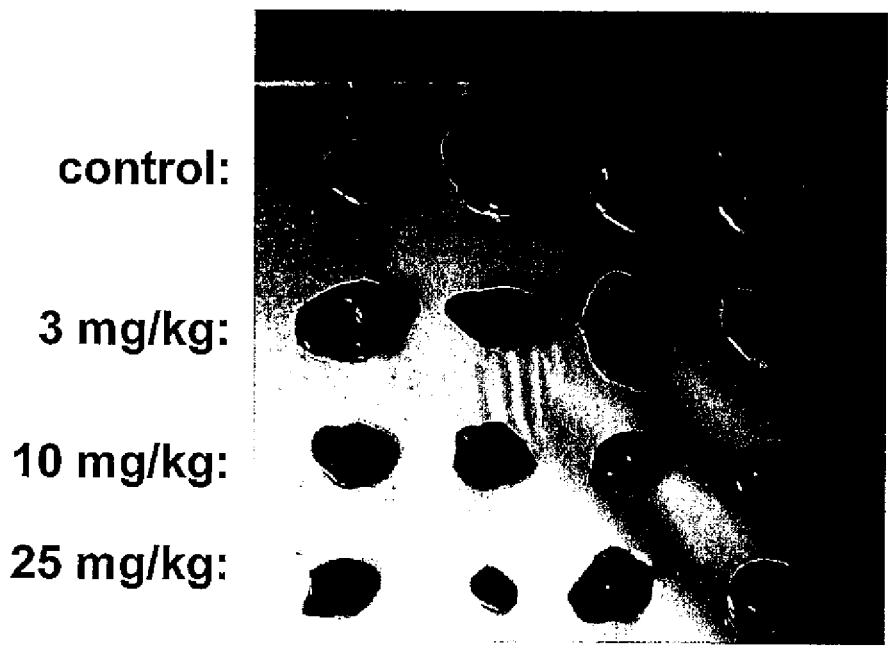

The results of analog-f9 are shown in FIGS. 7(a) and (b). The results of analog-k13 are shown in FIGS. 8(a) and (b). (a) is a graph showing the tumor weight of each group, and (b) is a photograph of isolated tumors. These are common in FIGS.

7 and 8. As is clear from FIGS. 7(a) and (b), the tumor weights of the 10 mg/kg and 25 mg/kg analog-f9 administration groups were reduced to 29% and 18% of that of the control group, respectively. Thus, analog-k9 showed marked antitumor activity. As is clear from FIGS. 8(a) and (b), the tumor weights of the 3 mg/kg, 10 mg/kg and 25 mg/kg analog-k13 administration groups were reduced to 70%, 41% and 28% of that of the control group, respectively. Thus, analog-k13 showed marked antitumor activity. In no administration groups, regardless of the kind of test compound, weight loss or diarrhea, or visual abnormalities in organs of the mice were observed.

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literatures cited in the above description are incorporated herein by reference.

The invention claimed is:

1. A compound represented by the general formula (C):

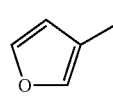

wherein $R^{101}$ represents a substituted or unsubstituted furyl group or a substituted or unsubstituted thienyl group, $R_{102}$, $R^{103}$, $R^{104}$ and $R^{105}$ may be the same or different, and each represents a hydrogen atom, a halogen atom, an alkyl group having 1 to 3 carbon atoms, or a haloalkyl group having 1 to 3 carbon atoms, and $R^{106}$ represents a hydrogen atom, or a saturated or unsaturated hydrocarbon group which is a straight or branched chain having 1 to 12 carbon atoms, but excluded is the case where when $R^{101}$ is a 3-furyl group, and $R^{102}$, $R^{103}$, $R^{104}$ and $R^{105}$ are all methyl groups, $R^{106}$ is not a methyl group, a 4-methyl-3-pentenyl group or a 4,8-dimethyl-3,7-nonadienyl group; or a pharmaceutically acceptable salt thereof.

2. The compound according to claim 1, wherein $R^{106}$ is a methyl group, a 4-methyl-3-pentenyl group or a 3-butynyl group; or a pharmaceutically acceptable salt thereof.

3. The compound according to claim 1, which is represented by formula (II):

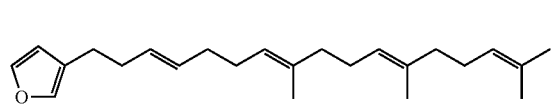

formula (III):

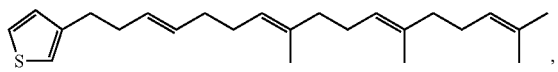

formula (VI):

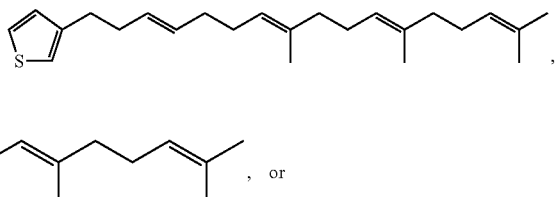, or formula (CI):

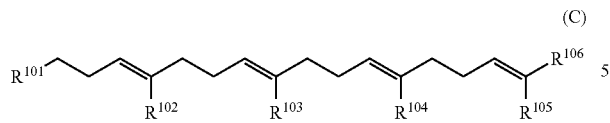

a pharmaceutically acceptable salt thereof.

4. The compound according to claim 1, wherein $R^{101}$ represents an unsubstituted furyl group or an unsubstituted thienyl group; or a pharmaceutically acceptable salt thereof.

5. A pharmaceutical composition comprising a compound according to claim 1 or a pharmaceutically acceptable salt thereof, and a pharmaceutically acceptable carrier.

6. An inhibitor of insulin-like growth factor 2 expression, comprising a compound according to claim 1 or a pharmaceutically acceptable salt thereof.

7. A selective inhibitor of hypoxic cell growth, comprising a compound according to claim 1 or a pharmaceutically acceptable salt thereof.

8. A medicament for cancer prevention or treatment, comprising a compound according to claim 1 or a pharmaceutically acceptable salt thereof.

9. The medicament according to claim 8, further comprising a chemotherapeutic drug, an immunotherapeutic drug or a hormone therapy drug.

10. The medicament according to claim 8, for use in combination with radiotherapy.

11. A compound represented by the general formula (I):

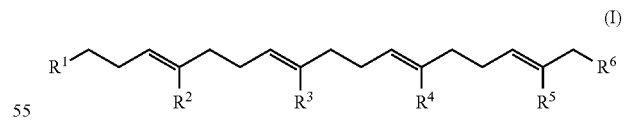

wherein $R^1$ represents a substituted or unsubstituted furyl group or a substituted or unsubstituted thienyl group, $R^2$, $R^3$, $R^4$ and $R^5$ may be the same or different, and each represents a hydrogen atom, a halogen atom, an alkyl group having 1 to 3 carbon atoms, or a haloalkyl group having 1 to 3 carbon atoms, and $R^6$ represents a hydrogen atom or a prenyl group, but excluded is the case where when $R^1$ is a 3-furyl group, then $R^2$, $R^3$, $R^4$ and $R^5$ are not all methyl groups or a pharmaceutically acceptable salt thereof.

* * * * *